US011783919B2

(12) United States Patent
Paradarami et al.

(10) Patent No.: US 11,783,919 B2
(45) Date of Patent: Oct. 10, 2023

(54) FORMATTING AND STORAGE OF GENETIC MARKERS

(71) Applicant: 23andMe, Inc., Sunnyvale, CA (US)

(72) Inventors: Tulasi Krishna Paradarami, San Ramon, CA (US); Michael Polcari, San Francisco, CA (US); Yeshwanth Bashyam Balachander, Sunnyvale, CA (US); Matthew Bryan Corley, Redwood City, CA (US); Anuved Verma, San Jose, CA (US); Anja Bog, Mountain View, CA (US); Cordell T. Blakkan, San Francisco, CA (US); Dmitry Stupakov, Moraga, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

(21) Appl. No.: 17/450,417

(22) Filed: Oct. 8, 2021

(65) Prior Publication Data
US 2022/0115139 A1 Apr. 14, 2022

Related U.S. Application Data

(60) Provisional application No. 63/198,315, filed on Oct. 9, 2020.

(51) Int. Cl.
*G16B 50/30* (2019.01)
*G16H 50/20* (2018.01)
*G16H 50/30* (2018.01)
*G16B 20/00* (2019.01)
*G16B 50/00* (2019.01)

(52) U.S. Cl.
CPC ............ *G16B 50/30* (2019.02); *G16B 20/00* (2019.02); *G16B 50/00* (2019.02); *G16H 50/20* (2018.01); *G16H 50/30* (2018.01)

(58) Field of Classification Search
CPC .................. G16B 50/00; G16B 50/30
USPC .................................................. 705/2
See application file for complete search history.

(56) References Cited

U.S. PATENT DOCUMENTS

| 7,797,302 B2 | 9/2010 | Kenedy et al. |
| 7,818,310 B2 | 10/2010 | Kenedy et al. |
| 7,844,609 B2 | 11/2010 | Kenedy et al. |
| 7,917,438 B2 | 3/2011 | Kenedy et al. |
| 7,933,912 B2 | 4/2011 | Kenedy et al. |

(Continued)

FOREIGN PATENT DOCUMENTS

| WO | WO2016/073953 | 5/2016 | |
| WO | WO-2017125778 A1 * | 7/2017 | ............ G06F 17/18 |
| WO | WO-2019126348 A1 * | 6/2019 | |

OTHER PUBLICATIONS

Mark, Adam Malka'i; Building biomedical infrastructure for aggregating variant annotation and prioritizing disease variants; San Diago State University, ProQuest Dissertation Publishing, 2015, 1593235 (Year: 2015).*

(Continued)

*Primary Examiner* — Hiep V Nguyen
(74) *Attorney, Agent, or Firm* — McDonnell Boehnen Hulbert & Berghoff LLP; David K. Buckingham

(57) ABSTRACT

The disclosed embodiments concern methods, apparatus, systems, and computer program products for storing and retrieving genetic data for individuals. In some implementations, a storage format is provided that allows genetic data to be defined by metadata for reproduce-ability.

24 Claims, 12 Drawing Sheets

(56) References Cited

U.S. PATENT DOCUMENTS

| | | |
|---|---|---|
| 7,941,329 B2 | 5/2011 | Kenedy et al. |
| 7,941,434 B2 | 5/2011 | Kenedy et al. |
| 7,957,907 B2 | 6/2011 | Sorenson et al. |
| 8,024,348 B2 | 9/2011 | Kenedy et al. |
| 8,051,033 B2 | 11/2011 | Kenedy et al. |
| 8,055,643 B2 | 11/2011 | Kenedy et al. |
| 8,065,324 B2 | 11/2011 | Kenedy et al. |
| 8,099,424 B2 | 1/2012 | Kenedy et al. |
| 8,108,406 B2 | 1/2012 | Kenedy et al. |
| 8,185,461 B2 | 5/2012 | Kenedy et al. |
| 8,187,811 B2 | 5/2012 | Eriksson et al. |
| 8,200,509 B2 | 6/2012 | Kenedy et al. |
| 8,209,319 B2 | 6/2012 | Kenedy et al. |
| 8,224,835 B2 | 7/2012 | Kenedy et al. |
| 8,255,403 B2 | 8/2012 | Kenedy et al. |
| 8,326,648 B2 | 12/2012 | Kenedy et al. |
| 8,386,519 B2 | 2/2013 | Kenedy et al. |
| 8,428,886 B2 | 4/2013 | Wong et al. |
| 8,452,619 B2 | 5/2013 | Kenedy et al. |
| 8,458,097 B2 | 6/2013 | Kenedy et al. |
| 8,458,121 B2 | 6/2013 | Kenedy et al. |
| 8,463,554 B2 | 6/2013 | Hon et al. |
| 8,510,057 B1 | 8/2013 | Avey et al. |
| 8,543,339 B2 | 9/2013 | Wojcicki et al. |
| 8,589,437 B1 | 11/2013 | Khomenko et al. |
| 8,606,761 B2 | 12/2013 | Kenedy et al. |
| 8,645,343 B2 | 2/2014 | Wong et al. |
| 8,655,899 B2 | 2/2014 | Kenedy et al. |
| 8,655,908 B2 | 2/2014 | Kenedy et al. |
| 8,655,915 B2 | 2/2014 | Kenedy et al. |
| 8,738,297 B2 | 5/2014 | Sorenson et al. |
| 8,786,603 B2 | 7/2014 | Rasmussen et al. |
| 8,788,283 B2 | 7/2014 | Kenedy et al. |
| 8,788,286 B2 | 7/2014 | Kenedy et al. |
| 8,855,935 B2 | 10/2014 | Myres et al. |
| 8,990,250 B1 | 3/2015 | Chowdry et al. |
| 9,031,870 B2 | 5/2015 | Kenedy et al. |
| 9,116,882 B1 | 8/2015 | Macpherson et al. |
| 9,170,992 B2 | 10/2015 | Kenedy et al. |
| 9,213,944 B1 | 12/2015 | Do et al. |
| 9,213,947 B1 | 12/2015 | Do et al. |
| 9,218,451 B2 | 12/2015 | Wong et al. |
| 9,336,177 B2 | 5/2016 | Hawthorne et al. |
| 9,367,663 B2 | 6/2016 | Deciu et al. |
| 9,367,800 B2 | 6/2016 | Do et al. |
| 9,390,225 B2 | 7/2016 | Barber et al. |
| 9,405,818 B2 | 8/2016 | Chowdry et al. |
| 9,582,647 B2 | 2/2017 | Kenedy et al. |
| 9,836,576 B1 | 12/2017 | Do et al. |
| 9,864,835 B2 | 1/2018 | Avey et al. |
| 9,977,708 B1 | 5/2018 | Do et al. |
| 10,025,877 B2 | 7/2018 | Macpherson |
| 10,162,880 B1 | 12/2018 | Chowdry et al. |
| 10,275,569 B2 | 4/2019 | Avey et al. |
| 10,296,847 B1 | 5/2019 | Do et al. |
| 10,379,812 B2 | 8/2019 | Kenedy et al. |
| 10,432,640 B1 | 10/2019 | Hawthorne et al. |
| 10,437,858 B2 | 10/2019 | Naughton et al. |
| 10,516,670 B2 | 12/2019 | Hawthorne et al. |
| 10,572,831 B1 | 2/2020 | Do et al. |
| 10,643,740 B2 | 5/2020 | Avey et al. |
| 10,658,071 B2 | 5/2020 | Do et al. |
| 10,691,725 B2 | 6/2020 | Naughton et al. |
| 10,699,803 B1 | 6/2020 | Do et al. |
| 10,755,805 B1 | 8/2020 | Do et al. |
| 10,777,302 B2 | 9/2020 | Chowdry et al. |
| 10,790,041 B2 | 9/2020 | Macpherson et al. |
| 10,803,134 B2 | 10/2020 | Kenedy et al. |
| 10,841,312 B2 | 11/2020 | Hawthorne et al. |
| 10,854,318 B2 | 12/2020 | Macpherson et al. |
| 10,891,317 B1 | 1/2021 | Chowdry et al. |
| 10,896,233 B2 | 1/2021 | Kenedy et al. |
| 10,936,626 B1 | 3/2021 | Naughton et al. |
| 10,957,455 B2 | 3/2021 | Kenedy et al. |
| 10,991,467 B2 | 4/2021 | Kenedy et al. |
| 10,999,285 B2 | 5/2021 | Hawthorne et al. |
| 11,003,694 B2 | 5/2021 | Kenedy et al. |
| 11,031,101 B2 | 6/2021 | Hon et al. |
| 11,049,589 B2 | 6/2021 | Hon et al. |
| 2008/0131887 A1 | 6/2008 | Stephan et al. |
| 2008/0227063 A1 | 9/2008 | Kenedy et al. |
| 2008/0228043 A1 | 9/2008 | Kenedy et al. |
| 2008/0228410 A1 | 9/2008 | Kenedy et al. |
| 2008/0228451 A1 | 9/2008 | Kenedy et al. |
| 2008/0228677 A1 | 9/2008 | Kenedy et al. |
| 2008/0228698 A1 | 9/2008 | Kenedy et al. |
| 2008/0228699 A1 | 9/2008 | Kenedy et al. |
| 2008/0228700 A1 | 9/2008 | Kenedy et al. |
| 2008/0228701 A1 | 9/2008 | Kenedy et al. |
| 2008/0228702 A1 | 9/2008 | Kenedy et al. |
| 2008/0228704 A1 | 9/2008 | Kenedy et al. |
| 2008/0228705 A1 | 9/2008 | Kenedy et al. |
| 2008/0228706 A1 | 9/2008 | Kenedy et al. |
| 2008/0228708 A1 | 9/2008 | Kenedy et al. |
| 2008/0228722 A1 | 9/2008 | Kenedy et al. |
| 2008/0228753 A1 | 9/2008 | Kenedy et al. |
| 2008/0228756 A1 | 9/2008 | Kenedy et al. |
| 2008/0228757 A1 | 9/2008 | Kenedy et al. |
| 2008/0228765 A1 | 9/2008 | Kenedy et al. |
| 2008/0228766 A1 | 9/2008 | Kenedy et al. |
| 2008/0228767 A1 | 9/2008 | Kenedy et al. |
| 2008/0228768 A1 | 9/2008 | Kenedy et al. |
| 2008/0228797 A1 | 9/2008 | Kenedy et al. |
| 2008/0243843 A1 | 10/2008 | Kenedy et al. |
| 2009/0043752 A1 | 2/2009 | Kenedy et al. |
| 2009/0099789 A1 | 4/2009 | Stephan et al. |
| 2009/0112871 A1 | 4/2009 | Hawthorne et al. |
| 2009/0118131 A1 | 5/2009 | Avey et al. |
| 2009/0119083 A1 | 5/2009 | Avey et al. |
| 2010/0042438 A1 | 2/2010 | Moore et al. |
| 2010/0063830 A1 | 3/2010 | Kenedy et al. |
| 2010/0063835 A1 | 3/2010 | Kenedy et al. |
| 2010/0063865 A1 | 3/2010 | Kenedy et al. |
| 2010/0070292 A1 | 3/2010 | Kenedy et al. |
| 2010/0070455 A1 | 3/2010 | Halperin et al. |
| 2010/0076950 A1 | 3/2010 | Kenedy et al. |
| 2010/0076988 A1 | 3/2010 | Kenedy et al. |
| 2010/0169262 A1 | 7/2010 | Kenedy et al. |
| 2010/0169313 A1 | 7/2010 | Kenedy et al. |
| 2010/0169338 A1 | 7/2010 | Kenedy et al. |
| 2011/0078168 A1 | 3/2011 | Kenedy et al. |
| 2011/0184656 A1 | 7/2011 | Kenedy et al. |
| 2012/0270190 A1 | 10/2012 | Kenedy et al. |
| 2012/0270794 A1 | 10/2012 | Eriksson et al. |
| 2013/0332081 A1* | 12/2013 | Reese .................. G16B 20/00 702/19 |
| 2013/0345988 A1 | 12/2013 | Avey et al. |
| 2014/0006433 A1 | 1/2014 | Hon et al. |
| 2014/0032122 A1 | 1/2014 | Bader et al. |
| 2014/0067355 A1 | 3/2014 | Noto et al. |
| 2015/0066385 A1* | 3/2015 | Schnall-Levin ....... G16B 30/20 702/20 |
| 2015/0227610 A1 | 8/2015 | Chowdry et al. |
| 2015/0248473 A1 | 9/2015 | Kenedy et al. |
| 2015/0347566 A1 | 12/2015 | Kenedy et al. |
| 2016/0026755 A1 | 1/2016 | Byrnes et al. |
| 2016/0048577 A1* | 2/2016 | Hall .................... G06F 16/248 707/737 |
| 2016/0103950 A1 | 4/2016 | Myres et al. |
| 2016/0171155 A1 | 6/2016 | Do et al. |
| 2016/0277408 A1 | 9/2016 | Hawthorne et al. |
| 2016/0350479 A1 | 12/2016 | Han et al. |
| 2017/0011042 A1 | 1/2017 | Kermany et al. |
| 2017/0017752 A1 | 1/2017 | Noto et al. |
| 2017/0053089 A1 | 2/2017 | Kenedy et al. |
| 2017/0185719 A1 | 6/2017 | Kenedy et al. |
| 2017/0220738 A1 | 8/2017 | Barber et al. |
| 2017/0228498 A1 | 8/2017 | Hon et al. |
| 2017/0277827 A1 | 9/2017 | Granka et al. |
| 2017/0277828 A1 | 9/2017 | Avey et al. |
| 2017/0286594 A1 | 10/2017 | Reid et al. |
| 2017/0329866 A1 | 11/2017 | Macpherson |
| 2017/0329891 A1 | 11/2017 | Macpherson et al. |
| 2017/0329899 A1 | 11/2017 | Bryc et al. |

(56) References Cited

U.S. PATENT DOCUMENTS

| | | |
|---|---|---|
| 2017/0329901 A1 | 11/2017 | Chowdry et al. |
| 2017/0329902 A1 | 11/2017 | Bryc et al. |
| 2017/0329904 A1 | 11/2017 | Naughton et al. |
| 2017/0329915 A1 | 11/2017 | Kittredge et al. |
| 2017/0329924 A1 | 11/2017 | Macpherson et al. |
| 2017/0330358 A1 | 11/2017 | Macpherson et al. |
| 2018/0181710 A1 | 6/2018 | Avey et al. |
| 2018/0307778 A1 | 10/2018 | Macpherson |
| 2019/0012431 A1 | 1/2019 | Hon et al. |
| 2019/0034163 A1 | 1/2019 | Kenedy et al. |
| 2019/0050437 A1* | 2/2019 | Goyal ................ G06F 16/2272 |
| 2019/0114219 A1 | 4/2019 | Do et al. |
| 2019/0130998 A1 | 5/2019 | Van Rooyen et al. |
| 2019/0139623 A1 | 5/2019 | Bryc et al. |
| 2019/0206512 A1 | 7/2019 | Lu et al. |
| 2019/0206514 A1 | 7/2019 | Avey et al. |
| 2019/0267115 A1 | 8/2019 | Avey et al. |
| 2019/0281061 A1 | 9/2019 | Hawthorne et al. |
| 2019/0384777 A1 | 12/2019 | Naughton et al. |
| 2020/0137063 A1 | 4/2020 | Hawthorne et al. |
| 2020/0210143 A1 | 7/2020 | Kenedy et al. |
| 2020/0372974 A1 | 11/2020 | Chowdry et al. |
| 2021/0020266 A1 | 1/2021 | Freyman et al. |
| 2021/0043278 A1 | 2/2021 | Hon et al. |
| 2021/0043279 A1 | 2/2021 | Hon et al. |
| 2021/0043280 A1 | 2/2021 | Hon et al. |
| 2021/0043281 A1 | 2/2021 | Macpherson et al. |
| 2021/0058398 A1 | 2/2021 | Hawthorne et al. |
| 2021/0074385 A1 | 3/2021 | Hon et al. |
| 2021/0082167 A1 | 3/2021 | Jewett et al. |
| 2021/0166452 A1 | 6/2021 | Jewett et al. |
| 2021/0166823 A1 | 6/2021 | Kenedy et al. |
| 2021/0193257 A1 | 6/2021 | Freyman et al. |
| 2021/0209134 A1 | 7/2021 | Kenedy et al. |
| 2021/0225458 A1 | 7/2021 | Hon et al. |
| 2021/0233665 A1 | 7/2021 | Kenedy et al. |
| 2021/0250357 A1 | 8/2021 | Hawthorne et al. |

OTHER PUBLICATIONS

International Search Report and Written Opinion issued in PCT Application No. PCT/US2021/054300 dated Feb. 18, 2022.

Verma, et al., "Imputation and quality control steps for combining multiple genome-wide datasets," Frontiers in Genetics, Dec. 11, 2014, pp. 1-15.

Ailamaki, A., "A Storage Model to Bridge the Processor/Memory Speed Gap," Carnegie Mellon University, Submission to HPTS 2001, pp. 1-5.

"The Variant Call Format (VCF) Version 4.2 Specification," downloaded from https://github.com/samtools/hts-specs. Jul. 27, 2021, pp. 1-29.

Bycroft, C., et al., "The UK Biobank resource with deep phenotyping and genomic data," Nature, Oct. 11, 2018, vol. 562, 25 pages.

Band, G., et al., "BGEN: a binary file format for imputed genotype and haplotype Data," Wellcome Centre for Human Genetics, University of Oxford, May 2, 2018, pp. 1-6.

* cited by examiner

Metadata

```
##fileformat=VCFv4.2
##fileDate=20090805
##source=myImputationProgramV3.1
##reference=file:///seq/references/1000GenomesPilot-NCBI36.fasta
##contig=<ID=20,length=62435964,assembly=B36,md5=f126cdf8a6e0c7f79d618ff66beb2da,species="Homo sapiens",taxonomy=x>
##phasing=partial
##INFO=<ID=NS,Number=1,Type=Integer,Description="Number of Samples With Data">
##INFO=<ID=DP,Number=1,Type=Integer,Description="Total Depth">
##INFO=<ID=AF,Number=A,Type=Float,Description="Allele Frequency">
##INFO=<ID=AA,Number=1,Type=String,Description="Ancestral Allele">
##INFO=<ID=DB,Number=0,Type=Flag,Description="dbSNP membership, build 129">
##INFO=<ID=H2,Number=0,Type=Flag,Description="HapMap2 membership">
##FILTER=<ID=q10,Description="Quality below 10">
##FILTER=<ID=s50,Description="Less than 50% of samples have data">
##FORMAT=<ID=GT,Number=1,Type=String,Description="Genotype">
##FORMAT=<ID=GQ,Number=1,Type=Integer,Description="Genotype Quality">
##FORMAT=<ID=DP,Number=1,Type=Integer,Description="Read Depth">
##FORMAT=<ID=HQ,Number=2,Type=Integer,Description="Haplotype Quality">
```

Header

| #CHROM | POS | ID | REF | ALT | QUAL | FILTER | INFO | FORMAT | NA00001 | NA00002 | NA00003 |
|---|---|---|---|---|---|---|---|---|---|---|---|
| 20 | 14370 | rs6054257 | G | A | 29 | PASS | NS=3;DP=14;AF=0.5;DB;H2 | GT:GQ:DP:HQ | 0\|0:48:1:51,51 | 1\|0:48:8:51,51 | 1/1:43:5... |
| 20 | 17330 | . | T | A | 3 | q10 | NS=3;DP=11;AF=0.017 | GT:GQ:DP:HQ | 0\|0:49:3:58,50 | 0\|1:3:5:65,3 | 0/0:41:3 |
| 20 | 1110696 | rs6040355 | A | G,T | 67 | PASS | NS=2;DP=10;AF=0.333,0.667;AA=T;DB | GT:GQ:DP:HQ | 1\|2:21:6:23,27 | 2\|1:2:0:18,2 | 2/2:35:4 |
| 20 | 1230237 | . | T | . | 47 | PASS | NS=3;DP=13;AA=T | GT:GQ:DP:HQ | 0\|0:54:7:56,60 | 0\|0:48:4:51,51 | 0/0:61:2 |
| 20 | 1234567 | microsat1 | GTC | G,GTCT | 50 | PASS | NS=3;DP=9;AA=G | GT:GQ:DP | 0/1:35:4 | 0/2:17:2 | 1/1:40:3 |

Data Lines

FIG. 1

Table Representation

| Row | Column A | Column B | Column C |
|---|---|---|---|
| 1 | A1 | B1 | C1 |
| 2 | A2 | B2 | C2 |
| 3 | A3 | B3 | C3 |
| 4 | A4 | B4 | C4 |
| 5 | A5 | B5 | C5 |
| 6 | A6 | B6 | C6 |

NSM:
| A1 | B1 | C1 | A2 | B2 | C2 | A3 | B3 | C3 |
| A4 | B4 | C4 | A5 | B5 | C5 | A6 | B6 | C6 |

DSM:
| A1 | A2 | A3 | A4 | A5 | A6 | B1 | B2 | B3 |
| B4 | B5 | B6 | C1 | C2 | C3 | C4 | C5 | C6 |

PAX / Parquet:

| Column Chunk 1 | | | Column Chunk 2 | | | Column Chunk 3 | | | Row Group 1 |
|---|---|---|---|---|---|---|---|---|---|
| A1 | A2 | A3 | B1 | B2 | B3 | C1 | C2 | C3 | |

| Column Chunk 1 | | | Column Chunk 2 | | | Column Chunk 3 | | | Row Group 2 |
|---|---|---|---|---|---|---|---|---|---|
| A4 | A5 | A6 | B4 | B5 | B6 | C4 | C5 | C6 | |

*FIG. 3*

FORMATTING AND STORAGE OF GENETIC MARKERS

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in their entireties and for all purposes.

BACKGROUND

Bioinformatics can include retrieving and processing genetic data for millions of individuals each having genetic data comprising millions of markers. Some analyses may be directed at analyzing genetic data of some of the individuals or analyzing a subset of genetic data of some of the individuals. Genetic data, including imputed genetic data, may be stored and retrieved for analysis and model generation.

The background description provided herein is for the purposes of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Disclosed herein are methods and systems of storing and retrieving genetic data, including imputed genetic data, for a large number of individuals. In one aspect of the embodiments herein, a method is presents for providing information from one or more files to a database having a table with at least about 20 million columns, the method including: receiving one or more Variant Call Format (VCF) or Binary Variant Call Format (BCF) files including imputed genetic data for one or more individuals, wherein the imputed genetic data is in a columnar format, wherein the imputed genetic data includes greater than about 20 million markers for each of the one or more individuals, wherein the greater than about 20 million markers are in sequential order; transposing the imputed genetic data from the one or more VCF or BCF files for each of the one or more individuals from columnar format to a plurality of rows, wherein the imputed genetic data for each of the one or more individuals is included in a row for the corresponding individuals; and saving the transposed imputed genetic data in a database with a unique column corresponding to each of the greater than about 20 million markers for each of the one or more individuals and a unique row for each of the one or more individuals. In some embodiments, the imputed genetic data includes greater than about 50 million markers for each of the one or more individuals. In some embodiments, the imputed genetic data includes greater than about 100 million markers for each of the one or more individuals. In some embodiments, the imputed genetic data includes greater than about 200 million markers for each of the one or more individuals. In some embodiments, the imputed genetic data includes greater than about 300 million markers for each of the one or more individuals. In some embodiments, the database includes greater than about 10 million individuals and greater than about 10 million rows. In some embodiments, the database includes greater than about 10 million individuals and greater than about 20 million rows. In some embodiments, the database includes greater than about 10 million individuals and greater than about 30 million rows. In some embodiments, the method further includes accessing a row of user data for an individual and generating user facing content for the individual based on the accessed user data. In some embodiments, the method further includes accessing the database to identify genetic data for a plurality of the one or more individuals having one or more preselected phenotypes; assembling a cases cohort including a first plurality of individuals having the one or more preselected phenotypes; assembling a control cohort including a second plurality of individuals not in the cases cohort; and performing a genome wide association study (GWAS) based on the genetic data from the database for individuals in the cases cohort and control cohort.

In some embodiments, the method further includes, prior to receiving one or more VCF or BCF files, imputing the genetic data of the one or more individuals and saving the imputed data in the one or more VCF or BCF files. In some embodiments, saving the imputed data in the one or more VCF or BCF files is done in one or more batches. In some embodiments, saving the transposed imputed genetic data in the database is done in one or more batches. In some embodiments, the method further includes generating metadata based on an imputation process used to generate the imputed genetic data, including an imputation panel version used for the imputation process, and storing the metadata. In some embodiments, the method further includes (i) storing metadata based on the receiving, transposing, and storing steps, and (ii) saving the metadata in the database. In some embodiments, the database includes a plurality of tables having dimensions of at least about 1 million×1 million. In some embodiments, the method further includes receiving a request from a user to delete the user's genetic data; and responsive to the request from the user, updating metadata for the corresponding user's genetic data so that the user's genetic data is not used in future data processing activities. In some embodiments, the method further includes receiving a request from a user to delete the user's genetic data; and responsive to the request from the user, deleting or nulling the imputed genetic data for the corresponding user's data.

In another aspect of the embodiments herein, a system to provide information from one or more files to a database having a table with at least about 20 million columns is provided, the system including one or more processors and one or more memory devices configured to: receive one or more Variant Call Format (VCF) or Binary Variant Call Format (BCF) files including imputed genetic data for one or more individuals, wherein the imputed genetic data is in a columnar format, wherein the imputed genetic data includes greater than about 20 million markers for each of the one or more individuals, wherein the greater than about 20 million markers are in sequential order; transpose the imputed genetic data from the one or more VCF or BCF files for each of the one or more individuals from columnar format to a plurality of rows, wherein the imputed genetic data for each of the one or more individuals is included in a row for the corresponding individuals; and save the transposed imputed genetic data in a database with a unique column corresponding to each of the greater than about 20 million markers for each of the one or more individuals and a unique row for each of the one or more individuals. In some embodiments, the imputed genetic data includes greater than about 50 million markers for each of the one or more individuals. In some embodiments, the imputed genetic data includes greater than about 100 million markers for each of the one or more individuals. In some embodiments, the imputed genetic data includes greater than about 200 million markers for each of the one or more individuals. In some embodiments, the imputed genetic data includes greater than about 300 million markers for each of the one or more individuals. In some embodiments, the database includes greater than about 10 million individuals and greater than about 10 million rows. In some embodiments, the database includes greater than about 10 million individuals and greater than about 20 million rows. In some embodiments, the database includes greater than about 10 million individuals and greater than about 30 million rows. In some embodiments, the one or more processors and one or more memory devices are further configured to access a row of user data for an individual and generate user facing content for the individual based on the accessed user data.

In some embodiments, the one or more processors and one or more memory devices are further configured to: access the database to identify genetic data for a plurality of the one or more individuals having one or more preselected phenotypes; assemble a cases cohort including a first plurality of individuals having the one or more preselected phenotypes; assemble a control cohort including a second plurality of individuals not in the cases cohort; and perform a genome wide association study (GWAS) based on the genetic data from the database for individuals in the cases cohort and control cohort. In some embodiments, the one or more processors and one or more memory devices are further configured to, prior to receiving one or more VCF or BCF files, impute the genetic data of the one or more individuals and save the imputed data in the one or more VCF or BCF files. In some embodiments, saving the imputed data in the one or more VCF or BCF files is done in one or more batches. In some embodiments, saving the transposed imputed genetic data in the database is done in one or more batches. In some embodiments, the one or more processors and one or more memory devices are further configured to generate metadata based on an imputation process used to generate the imputed genetic data, including an imputation panel version used for the imputation process, and store the metadata. In some embodiments, the one or more processors and one or more memory devices are further configured to: (i) store metadata based on the receiving, transposing, and storing steps, and (ii) save the metadata in the database. In some embodiments, the database includes a plurality of tables having dimensions of at least about 1 million×1 million. In some embodiments, the one or more processors and one or more memory devices are further configured to: receive a request from a user to delete the user's genetic data; and responsive to the request from the user updating metadata for the corresponding user's genetic data so that the user's genetic data is not used in future data processing activities. In some embodiments, the one or more processors and one or more memory devices are further configured to: receive a request from a user to delete the user's genetic data; and responsive to the request from the user, deleting or nulling the imputed genetic data for the corresponding user's data.

In another aspect of the embodiments herein, a non-transient computer-readable medium is provided, the non-transient computer-readable medium including program instructions that, when executed by one or more processors, cause the one or more processors to: receive one or more Variant Call Format (VCF) or Binary Variant Call Format (BCF) files including imputed genetic data for one or more individuals, wherein the imputed genetic data is in a columnar format, wherein the imputed genetic data includes greater than about 20 million markers for each of the one or more individuals, wherein the greater than about 20 million markers are in sequential order; transpose the imputed genetic data from the one or more VCF or BCF files for each of the one or more individuals from columnar format to a plurality of rows, wherein the imputed genetic data for each of the one or more individuals is included in a row for the corresponding individuals; and save the transposed imputed genetic data in a database with a unique column corresponding to each of the greater than about 20 million markers for each of the one or more individuals and a unique row for each of the one or more individuals.

In some embodiments, the imputed genetic data includes greater than about 50 million markers for each of the one or more individuals. In some embodiments, the imputed genetic data includes greater than about 100 million markers for each of the one or more individuals. In some embodiments, the imputed genetic data includes greater than about 200 million markers for each of the one or more individuals. In some embodiments, the imputed genetic data includes greater than about 300 million markers for each of the one or more individuals. In some embodiments, the database includes greater than about 10 million individuals and greater than about 10 million rows. In some embodiments, the database includes greater than about 10 million individuals and greater than about 20 million rows. In some embodiments, the database includes greater than about 10 million individuals and greater than about 30 million rows. In some embodiments, the program instructions include further instructions that, when executed by one or more processors, cause the one or more processors to access a row of user data for an individual and generate user facing content for the individual based on the accessed user data. In some embodiments, the program instructions include further instructions that, when executed by one or more processors, cause the one or more processors to: access the database to identify genetic data for a plurality of the one or more individuals having one or more preselected phenotypes; assemble a cases cohort including a first plurality of individuals having the one or more preselected phenotypes; assemble a control cohort including a second plurality of individuals not in the cases cohort; and perform a genome wide association study (GWAS) based on the genetic data from the database for individuals in the cases cohort and control cohort.

In some embodiments, the program instructions include further instructions that, when executed by one or more processors, cause the one or more processors to, prior to receiving one or more VCF or BCF files, impute the genetic data of the one or more individuals and save the imputed data in the one or more VCF or BCF files. In some embodiments, saving the imputed data in the one or more VCF or BCF files is done in one or more batches. In some embodiments, saving the transposed imputed genetic data in the database is done in one or more batches. In some embodiments, the program instructions include further instructions that, when executed by one or more processors, cause the one or more processors to generate metadata based on an imputation process used to generate the imputed genetic data, including an imputation panel version used for the imputation process, and store the metadata. In some embodiments, the program instructions include further instructions that, when executed by one or more processors, cause the one or more processors to: (i) store metadata based on the receiving, transposing, and storing steps, and (ii) save the metadata in the database. In some embodiments, the database includes a plurality of tables having dimensions of at least about 1 million×1 million. In some embodiments, the program instructions include further instructions that, when executed by one or more processors, cause the one or more processors to: receive a request from a user to delete the user's genetic data; and responsive to the request from the user updating metadata for the corresponding user's genetic data so that the user's genetic data is not used in future data processing activities. In some embodiments, the program instructions include further instructions that, when executed by one or more processors, cause the one or more processors to: receive a request from a user to delete the user's genetic data; and responsive to the request from the user, deleting or nulling the imputed genetic data for the corresponding user's data.

In another aspect of the embodiments herein, a method of providing information from one or more files of a database having a table with at least about 20M columns is provided, the method including: receiving a request for a plurality of markers for each individual of about 10,000 or more individuals, wherein the plurality of markers is at least about 10,000 markers; retrieving metadata corresponding to a plurality of files, wherein each file stores a continuous set of markers for a batch of samples, wherein the continuous set of markers is less than about 10,000 markers; accessing the plurality of files based on the request and the metadata corresponding to the plurality of files; and providing the plurality of markers for each of the about 10,000 or more individuals. In some embodiments, the request further includes a datetime, and the method further includes: identifying a first set of samples that are prior to the datetime; and providing the plurality of markers for each of the one or more individuals based on the first set of samples. In some embodiments, the first set of samples includes a first sample and a second sample, the first sample and the second sample corresponding to a first individual of the one or more individuals, wherein the method further includes: determining that the second sample was determined later than the first sample; and providing the plurality of markers for the first individual based on the second sample. In some embodiments, the batch of samples is at least 100,000 samples. In some embodiments, the files are parquet files. In some embodiments, the plurality of markers is at least about 1 million markers.

In another aspect of the embodiments herein, a system to provide information from one or more files of a database having a table with at least about 20M columns is provided, the system including one or more processors and one or more memory devices configured to: receive a request for a plurality of markers for each individual of about 10,000 or more individuals, wherein the plurality of markers is at least about 10,000 markers; retrieve metadata corresponding to a plurality of files, wherein each file stores a continuous set of markers for a batch of samples, wherein the continuous set of markers is less than about 10,000 markers; access the plurality of files based on the request and the metadata corresponding to the plurality of files; and provide the plurality of markers for each of the about 10,000 or more individuals. In some embodiments, the request further includes a datetime, and wherein the one or more processors and one or more memory devices are further configured to: identify a first set of samples that are prior to the datetime; and provide the plurality of markers for each of the one or more individuals based on the first set of samples. In some embodiments, the first set of samples includes a first sample and a second sample, the first sample and the second sample corresponding to a first individual of the one or more individuals, wherein the one or more processors and one or more memory devices are further configured to: determine that the second sample was determined later than the first sample; and provide the plurality of markers for the first individual based on the second sample. In some embodiments, the batch of samples is at least 100,000 samples. In some embodiments, the files are parquet files. In some embodiments, the plurality of markers is at least about 1 million markers.

In another aspect of the embodiments herein, a non-transient computer-readable medium is provided, the non-transient computer-readable medium including program instructions that, when executed by one or more processors, cause the one or more processors to: receive a request for a plurality of markers for each individual of about 10,000 or more individuals, wherein the plurality of markers is at least about 10,000 markers; retrieve metadata corresponding to a plurality of files, wherein each file stores a continuous set of markers for a batch of samples, wherein the continuous set of markers is less than about 10,000 markers; access the plurality of files based on the request and the metadata corresponding to the plurality of files; and provide the plurality of markers for each of the about 10,000 or more individuals. In some embodiments, the request further includes a datetime, and wherein the program instructions include further instructions that, when executed by one or more processors, cause the one or more processors to: identify a first set of samples that are prior to the datetime; and provide the plurality of markers for each of the one or more individuals based on the first set of samples. In some embodiments, the first set of samples includes a first sample and a second sample, the first sample and the second sample corresponding to a first individual of the one or more individuals, wherein the program instructions include further instructions that, when executed by one or more processors, cause the one or more processors to: determine that the second sample was determined later than the first sample; and provide the plurality of markers for the first individual based on the second sample. In some embodiments, the batch of samples is at least 100,000 samples. In some embodiments, the files are parquet files. In some embodiments, the plurality of markers is at least about 1 million markers.

These and other features of the disclosed embodiments will be described in detail below with reference to the associated drawings.

BRIEF DESCRIPTION OF DRAWINGS

FIG. 1 presents an example variant call format (VCF) file.

FIG. 3 presents a visual representation of various storage models described herein.

DETAILED DESCRIPTION

Terminology

Figure 2:
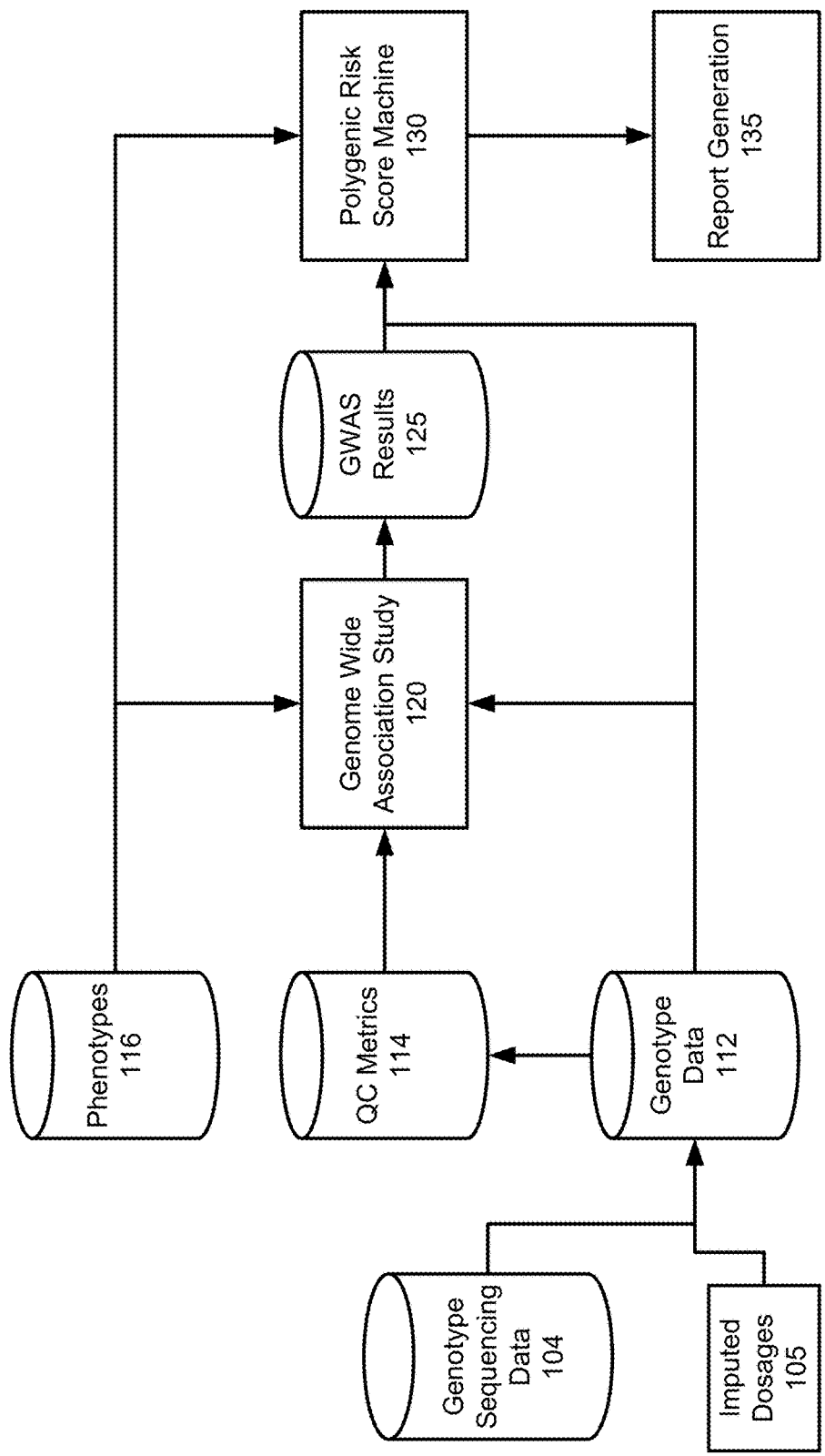
FIG. 2 is a schematic illustration of different data storage and processing modules described herein.

"Dosage" refers to the predicted dosage of the non-reference allele given the data available; it will typically have a value between 0 and 2. Thus, for a given individual, a genetic marker will have a value of 0 to 2. If the marker has only reference alleles, the dosage is 0; if the marker has one reference allele and one variant allele, the dosage is 1; and if the marker has two variant alleles, the dosage is 2. For imputed genetic information, a marker may have a non-integer value, in some implementations between 0 and 2. The non-integer value may be based on statistical assessments conducted using an imputation protocol.

"Marker" or single nucleotide polymorphism ("SNP") refers to variations in a single DNA nucleotide between people.

"Gene sequence variations file" refers to files that store gene sequence variation data. The systems and methods described herein can use various genetic data file format types. While the present disclosure primarily uses the Variant call format (VCF) as an example, other examples of files can be used like the binary variant call format (BCF), GEN, and binary GEN (BGEN) format. Typically, such formats store information about markers in a vertical format, with information about each marker being presented in a separate row.

"Variant Call Format" (VCF) is a specification for formatting used in bioinformatics for storing gene sequence variations, typically in a compressed text file. According to the VCF specification, a VCF file has meta-information lines, a header line, and data lines. Compressed VCF files are indexed for fast data retrieval (random access) of variants from a range of positions. The complete specification for version 4.2 may be found at (https://samtools.github.io/hts-specs/VCFv4.2.pdf), which is incorporated herein for all purposes. For scalability and maintainability, VCF files are chunked by markers (typically, markers associated with a chromosome are stored in one file) and batched by samples. A common access pattern in genomic analysis retrieves genetic data for all samples at a given marker, and executing such a query requires scanning every batch of VCF files for a given chunk. FIG. 1 presents an example VCF file.

Apache Parquet (hereinafter referred to as "Parquet") is an open-source hybrid storage format that is useful for highly performant data I/O. Traditionally, data may be stored in a database using an n-ary storage model (NSM), where bytes associated with a given row are stored contiguously in a row-major orientation within data pages. While this format works well for queries that retrieve all or majority of the columns for a given predicate (for example, all markers for a given individual), it is not well suited for queries that typically access only a small subset of the columns (e.g., a chunk of markers for a large number of users). A decomposition storage model (DSM) is an alternative to NSM, where data is organized and stored in a columnar format. Column-major layout may optimize for disk I/O since this orientation of the data allows for scanning and retrieving only relevant parts of the data pages for analytical workloads. Fewer disk seeks and better compression (because the data type of a single column or column-chunk is homogenous) may lead to better query performance compared to a row-major layout. Furthermore, a columnar format also supports column-specific compression and/or encoding techniques that may further optimize I/O.

However, Both NSM and DSM suffer from certain limitations. Partition Attributes Across (PAX) (Ailamaki, Anastassia, "A Storage model to Bridge the Processor/Memory Speed Gap" available at http://www.hpts.ws/papers/2001/AnastassiaAilamaki.pdf, which is hereby incorporated herein for all purposes) is a hybrid storage model that addresses the limitations in NSM and DSM storage models. Parquet utilizes this hybrid storage model and combines the horizontal and vertical data partitioning strategies of NSM and DSM models such that data is organized into row groups and column chunks. While this application refers to a PAX implementation called Parquet, it should be understood that other PAX storage models may be used.

Apache Arrow (https://arrow.apache.org/) (hereinafter referred to as "Arrow") is an in-memory columnar serialization standard designed for performing highly efficient analytical operations by enabling O(1) random access to data and zero-copy reads. Arrow trades off mutability in favor of constant-time random access and data locality for read-heavy workloads. Since Arrow is written in C++, it provides a genuine multi-processing framework and does not suffer from the limitations of the Python GIL. Arrow specifies a standardized language-independent columnar memory format for flat and hierarchical data, organized for efficient analytical operations on modern hardware, and PyArrow (https://arrow.apache.org/docs/python/) provides Python Arrow bindings.

Introduction and Contextual Examples

This disclosure relates to systems and methods for efficiently storing genotype data for large numbers of individuals with or without imputed genetic data. Bioinformatics may include analyzing large amounts of genotype data for a large number of individuals. In some implementations, genotype data may be analyzed for determining models used to generate polygenic risk scores ("PRS" or "PGS") for individuals. In particular, Genome Wide Association Studies (GWAS) analyze genotype data for a large number of individuals to identify multiple genetic variants or SNPs with small to moderate impact on a phenotype of interest. These genetic variants may then be used, along with genotype data, to determine PRS models to generate PRS scores for individuals.

FIG. 2 presents a block diagram for a pipeline that stores and uses genotype data. The depicted processing modules may be configured to provide users with reports or other information about their health. A genotype sequencing data module 104 may comprise genotype data assayed from chips used to analyze samples from individuals. An imputed dosages module 105 may be configured to provide imputed genetic marker information. The sequenced genotypes and imputed dosages may be stored in a genotype data module 112. The genotype data module 112 may then provide dosages to other data storage and processing modules. For example, a genome wide association study (GWAS) logic 120 may receive dosages from module 112, quality control metric data from a quality control metrics module 114 (e.g., allow lists or don't allow lists for particular SNPs), and a target phenotype from phenotype module 116 (which may store data on phenotypes for each individual). GWAS logic 120 may then analyze the received data to produce a list of SNPs that are associated with the target phenotype, which may be stored in GWAS results module 125.

In some embodiments, performing a GWAS may comprise identifying cohorts of cases and controls for a given or preselected phenotype followed by pulling the dosages in vector form from the data storage systems described herein. The speed for pulling the vector with the dosages from the data storage systems described herein may be improved compared to prior art storage systems. Pulling the genetic marker information in all genetic markers for the GWAS analysis from the data systems described herein may be performed in a highly parallel and efficient manner. A GWAS analysis can then be performed using identified cohorts of cases and controls.

In some embodiments, the systems described herein can be used to perform a phenome wide association study (pheWAS). Performing a pheWAS may comprise identifying cohorts of cases and controls for a preselected genetic variant followed by pulling the phenotypic information for the cases and controls for analysis in the pheWAS. Pulling the information for the individuals in the cases and controls group for the pheWAS analysis from the data systems described herein may be performed in a highly parallel and efficient manner. A pheWAS analysis can then be performed using the identified cohorts of cases and controls and associated phenotypes.

Furthermore, dosages may be provided to a PRS machine module 130 (optionally trained by machine learning techniques) for generating polygenic risk score (PRS) models based on the genotype dosage data, the target phenotype, and the GWAS results (e.g., a list of SNPs associated with the target phenotype. After training, a PRS model may then be used in report generation module 135 to output a PRS for an individual. The speed for providing dosages to a PRS machine model, particularly for training a PRS model, may be improved using data storage systems described herein. Further discussion of the various modules and processes for performing a GWAS, training a PRS model, and using a PRS model may be found in U.S. patent application Ser. No. 17/303,398, titled "MACHINE LEARNING PLATFORM FOR GENERATING RISK MODELS" and filed May 27, 2021, which is hereby incorporated herein for all purposes.

In some embodiments, the depicted pipeline is configured to provide a high-performance service for storing and retrieving genetic data, such as dosages of large numbers of imputed variants for multiple samples (implemented as genotype data module 112) with imputed dosages in a parquet format. In some implementations, the pipeline will obtain imputed dosages from the results from a system for generating and/or storing imputed results (e.g., imputed dosages module 105). In some embodiments, the dosages (imputed and/or physically called) are made available for one or more GWAS or pheWAS. In some embodiments, the stored information includes imputation and/or other information for GWAS metadata. In some implementations, imputed dosages module 105 provides the flow responsible for imputing (creating the imputed dosage data for genotype data module 112 in a gene sequence variations file format, such as variant call format or binary call format (VCF/BCF) files in a cloud storage from raw genomic data) and populating imputed genotype dosages metadata. While the description herein is focused on VCF and BCF files, the systems and methods disclosed herein are not limited to VCF and BCF files. Other data and file types can be used with the methods and systems described herein.

In bioinformatics, data storage systems may be used for various use cases. For example, user facing content in a production environment may include accessing an entire set of markers for a given individual. Such access may be appropriate for user/customer requests for, e.g., PRS and reports about their own genetic information. Alternatively, data storage systems can be accessed to return all customers with a given attribute, such as SNP or combination of SNPs. This access may be appropriate for research requests for, e.g., identifying cohorts and GWAS purposes.

Variant Call Format (VCF) is a popular text file format for storing genetic variation data, and is the standard output for popular imputation methodologies like minimac. It is unambiguous, flexible, and supports arbitrary metadata. A drawback of the VCF format, however, is that it is a text file and it requires a lot of storage space, even with compression. Furthermore, for databases with millions of customers, performance of the query is slow because a large number of batches are scanned to retrieve data for all customers for a given marker. Performance of the query may be improved by indexing the VCF files, but the fundamental constraint with VCF files is that data is stored in a layout which is not optimal for fast genomic analysis.

Discussed herein are the benefits of using hybrid storage formats such as Apache Parquet for storing genetic data and/or imputed genetic data. A hybrid layout may improve compression, reducing file size, and improve read speed compared to a column-major layout such as VCF. In various implementations, transposing the VCF file schema such that samples are stored as rows and markers as columns brings it closer to a traditional database table schema that allows for appending/inserting new samples into the table as they are processed by the data pipelines. An extension of this schema is a column-major format, similar to Parquet. In practice, data in Parquet files is organized as column chunks and row groups such that genetic data for a given marker and a "set" of samples is stored as contiguous bytes. This format is optimized for the access pattern "retrieve all samples for a marker".

FIG. 3 presents illustrations of NSM, DSM, and PAX/Parquet storage formats. The Table Representation presents a logical schema of rows and columns. The NSM table presents a row-major format, where each column value for a given row is stored next to each other. The DSM table presents a column-major format, where all or multiple values from one column are stored next to each other. The PAX/Parquet table presents a hybrid format, where row groups are defined for a group of rows, and then column chunks store all column values from one column for the row group next to each other. A parquet file may comprise one or more row groups, and a single row group contains data for all columns for some number of rows (which may vary within a single parquet file). In some implementations a row group may include one data chunk for every column, and every data chunk may include one or more pages with column data.

Figure 4:
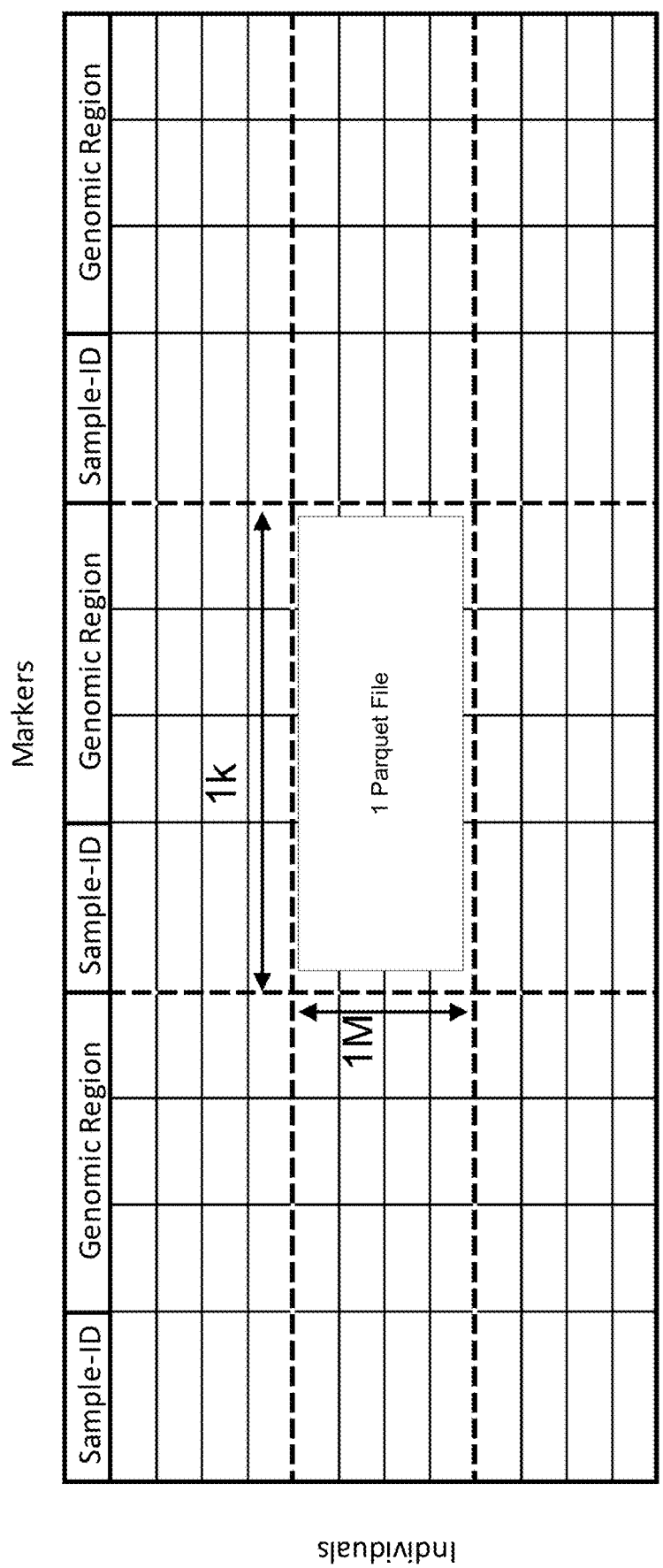
FIG. 4 illustrates the logical and physical schema of genotype data storage systems described herein.

FIG. 4 presents a physical schema of a parquet model for storing genomic data. For example, a logical table (e.g., 20 million (individuals/samples)×99 million (markers)) can be partitioned vertically by genomic regions. In some embodiments, rows are individuals represented by sample IDs. In some embodiments a sample ID may map to a single individual, but a single individual may be associated with multiple sample IDs (for example, multiple sequencing reads were performed or multiple imputation panels were applied such that the results of each read or imputation are stored separately). Each genomic region is responsible for storing "n" marker-major statistics. Examples of marker-major statistics include variants, markers, dosages (dosages from genotyping and/or imputation), and next generation sequencing (NGS) related data (read depth, quality scores, etc.). A genomic region may correspond to contiguous marker locations for a chromosome or group of chromosomes. The actual value of n can be derived empirically. Partitioning the table based on the genomic region also ensures the table width is manageable without losing the benefits of contiguous storage for dosages.

In some embodiments, a parquet file may comprise a row group of a first group of individuals. In FIG. 4 one million individuals are in a row group of a parquet file. Furthermore, a parquet file may comprise a first set of chunks of the marker data for the first group; in FIG. 4 one thousand markers are in a parquet file. In some embodiments each marker may be a column chunk. A plurality of parquet files may be used to store the marker data for all individuals, such that a first group of individuals may have multiple parquet files, each parquet file including columns for a marker or chunk of the marker data. A second group of individuals may then have genotype data represented by additional parquet files comprising a corresponding row group and column chunks for the second group of individuals.

While FIG. 4 illustrates dimensions of at least about 1 million samples and at least about 1000 markers per file, other dimensions are possible. Other dimensions of samples and markers per file can also be used for efficiency and storage reasons. In some implementations more than about 10,000 markers can be included per file, or between about 10,000 and 100,000 markers per file. In some implementations more than about 100,000 markers can be included per file. In some implementations less than about 100,000 markers can be included per file. In some implementations more than about 1,000,000 markers can be included per file, or between about 100,000 markers and about 1,000,000 markers per file. In some implementations at least about 100,000 samples may be included per file. In some implementations at least about 500,000 samples may be included per file. In some implementations at least about 2,000,000 samples may be included per file.

In some implementations, the markers may include imputed markers. Imputation generally refers to statistical inference of unobserved genotypes. Imputation may be performed using known haplotypes in a population. As noted above, while dosage for a marker that is directly sequenced may be 0, 1, or 2, an imputed dosage may have a non-integer value reflecting the statistical analysis performed using an imputation panel. An example of the non-integer value can include a frequency or probability for one or more alleles at a particular marker.

In some implementations the imputed dosages module 105 may receive the genotype data for one or more individuals (from a chip or other physical genotyping system) and process the data to impute additional markers that were not present in the original genotype data. An imputation panel can include proprietary 23andMe imputation algorithms alone or in combination with publicly available imputation panels. Further discussion of imputation algorithms and methods may be found in U.S. patent application Ser. No. 13/908,455, titled "IDENTIFYING VARIANTS OF INTEREST BY IMPUTATION" and filed Jun. 3, 2013, which is hereby incorporated herein for all purposes. The number of imputed markers based on the original genotype data is constantly increasing and improving with the addition of full sequence data of additional individuals and algorithmic improvements. The bead chip genotyping chip can include on the order of around 1,000,000 markers. In one implementation a current bead chip genotyping chip has around 1,500,000 markers. Each marker usually includes two alleles or variants but in triallelic markers there are three alleles or variants. Imputation can add a significant number of markers. In some implementations the number of imputed markers based on the genotype data exceeds 20,000,000 markers. In some implementations the number of imputed markers based on the genotype data exceeds 50,000,000 markers. In some implementations the number of imputed markers based on the genotype data exceeds 75,000,000 markers. In some implementations the number of imputed markers based on the genotype data exceeds 100,000,000 markers. In some implementations the number of imputed markers based on the genotype data exceeds 125,000,000 markers. In some implementations the number of imputed markers based on the genotype data exceeds 150,000,000 markers. In some implementations the number of imputed markers based on the genotype data exceeds 200,000,000 markers. In some implementations the number of imputed markers based on the genotype data exceeds 250,000,000 markers. In some implementations the number of imputed markers based on the genotype data exceeds 300,000,000 markers. In some implementations the number of imputed markers based on the genotype data exceeds 400,000,000 markers. In some implementations the number of imputed markers based on the genotype data exceeds 500,000,000 markers. In some implementations the number of imputed markers based on the genotype data exceeds 1,000,000,000 markers. In some implementations the number of imputed markers based on the genotype data exceeds 1,500,000,000 markers. In some implementations the number of imputed markers based on the genotype data exceeds 2,000,000,000 markers. In some implementations the imputed dosages module is configured to transfer imputed markers to the genotype data module, which is configured to generate dosages and optionally store the marker data in a storage format as described herein. The actual genotype markers can be retrieved from a genotype sequencing data module 104. In some implementations the imputed dosages module is also configured to store the directly genotyped markers and transfer that data to the genotype data module.

In some implementations, the storage schema can include greater than 10 million rows with each row corresponding to a unique individual/customer or a unique sample (in implementations where multiple samples may correspond with a single individual). In some implementations the storage schema includes greater than 20 million rows with each row corresponding to a unique individual/customer. In some implementations the storage schema includes greater than 30 million rows with each row corresponding to a unique individual/customer. In some implementations the storage schema includes greater than 40 million rows with each row corresponding to a unique individual/customer. In some implementations the storage schema includes greater than 50 million rows with each row corresponding to a unique individual/customer.

Genotype dosages module 112 is a genetic dosage storage and retrieval module for supporting large-scale analyses suitable for, e.g., research purposes (similar to GWAS) and for customer facing applications such as applications for generating polygenic risk scores (PRS). In some implementations, a data pipeline may be configured to achieve one or more of the following features with the genotype dosages module:
  Import some or all of previously imputed dosages (e.g., imputed prior to deployment in the pipeline) from VCFs, BCFs, or other genetic data storage formats, processed by, e.g., the imputed dosages 105 module.
  Periodically import the newly imputed dosages from VCFs (or BCFs, etc.) processed by, e.g., the imputed dosages 105 module.

Provide an efficient imputed dosage storage and retrieval system capable of high read throughput, e.g., greater than about 10,000 requests per minute.

Provide a management system configured to return a "vector(s)" of dosages for a given variant/set of variants from the storage and retrieval system.

Scale to support a relatively small number of customers (e.g., about 1 million customers) and scale to much larger numbers of customers (e.g., about 20 million or more customers).

Efficiently access samples and markers.

Adapt the storage and retrieval system to modify the number of variants in a genomic region.

Decouple imputed data storage and access layers from GWAS-related activities.

Figure 5:
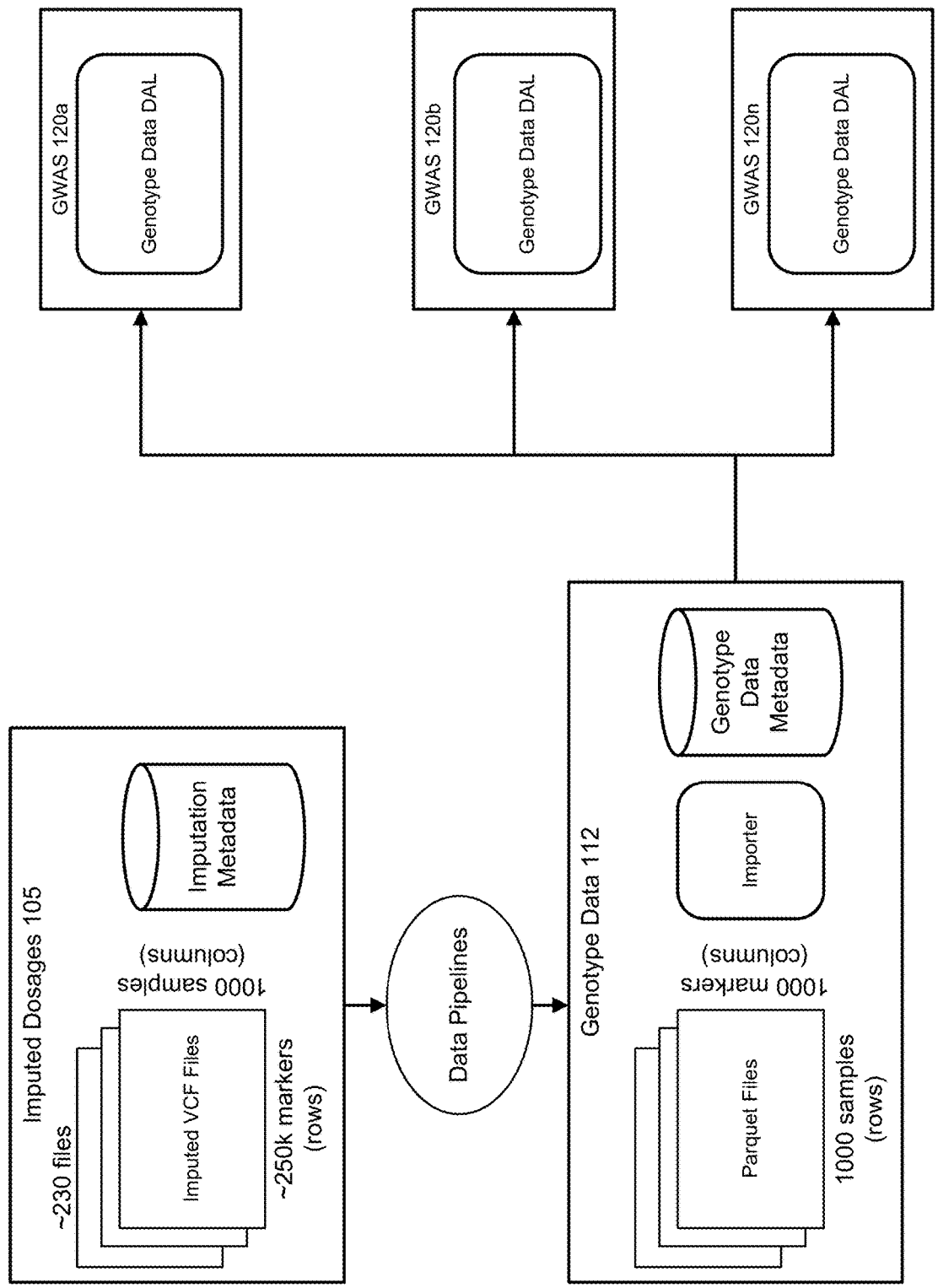
FIG. 5 is a schematic illustration of an imputation module, data pipelines, genetic data storage module, and client side interface with a data access layer (DAL) for downstream GWAS in accordance with some implementations.

In some implementations a Data Access Layer (DAL) may be responsible for abstracting out complexities of the underlying storage system (ex: genomic regions, metadata, etc.) and providing a simple interface to clients using the platform. FIG. 5 includes illustrations of how a DAL interacts with the imputed dosages module 105. A DAL, optionally interacting with another service/module such as genotype data module 112, may be configured to support GWASes 120a-n or other research queries to achieve one or more of the following:

Store required metadata to support the various GWAS query patterns.

Ensure reproducibility of GWAS results by supporting time-travel. "Time travel" can be achieved with metadata-driven time travel support. An explanation of certain time travel embodiments is presented below.

Build in regulatory and privacy compliance (GDPR compliance, etc.)

Data Pipeline Input (to Genotype Data Module)

In the depicted embodiments, the imputed dosages module is the source of data for the genotype data module pipeline. The imputed dosages module may generate imputed dosages for samples in batches of 1000 samples per batch. Different imputation panels can be used including public and proprietary imputation panels and combinations thereof. The results of each imputation batch may be stored in a cloud server, which may contain approximately 230 VCF files. In some implementations, the result of each imputation batch may be a set of BCF files, e.g., approximately 25 BCF files. Each batch of imputation files represents the dosages of all the imputed markers for the 1000 samples of that batch. Other batch sizes may be employed. For example, batch sizes of between about 5 to about 5000 samples may be analyzed for imputation.

Data Pipeline Output (from Genotype Data Module)

The pipeline writes dosages in parquet format stored in a cloud server or other storage. In some implementations the outputs are grouped into genomic regions where each region contains 1000 markers. The output parquet may have markers as columns and samples as rows as shown in FIG. 4. Each genomic region can have a different schema as they have a different set of markers as columns.

Figure 6:
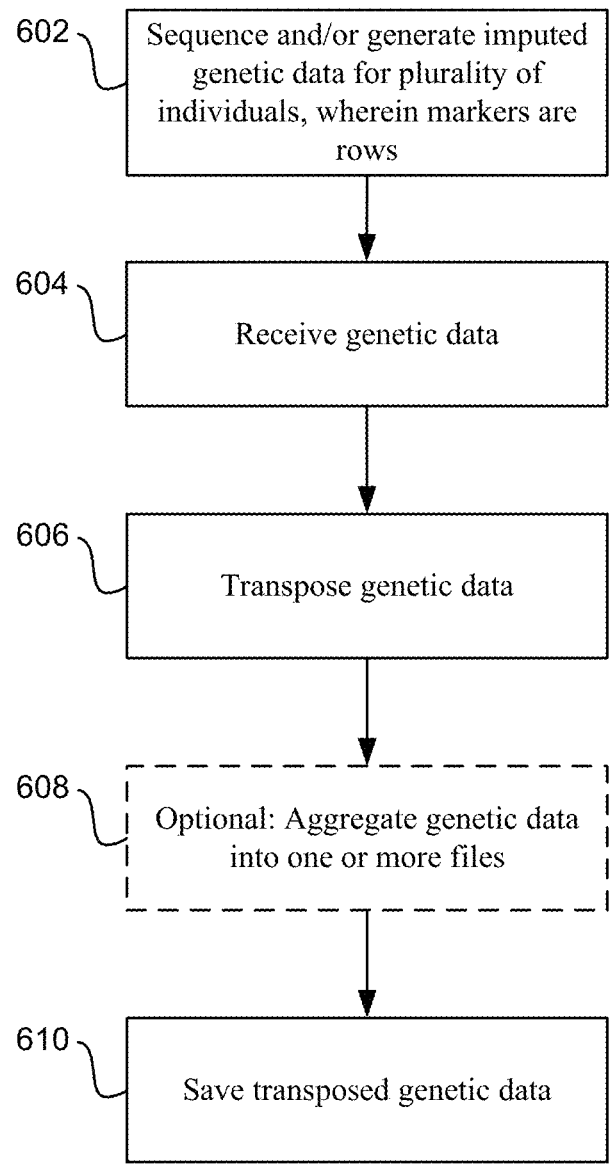
FIG. 6 illustrates a flow chart for importing batches of data into parquet formats according to some implementations.

FIG. 6 presents a flowchart for transposing genetic data to a format having markers as columns and samples as rows, as described herein. In operation 602, samples are physically called and/or imputed markers (and when present, associated allele variants or the likelihood of their presence) are generated for samples that have had some markers physically called. In operation 604, the imputed markers (optionally along with physically called markers) is received in a standard format such as a VCF or BCF format. In some implementations the imputed markers are received in a gene sequences variation file that is not in a PAX or parquet format. In operation 606, the imputed marker data (optionally along with physically called marker data) is converted/transposed from the standard format to marker dosages in a parquet format. Operation 608 is an optional operation to aggregate genetic data into one or more files. As discussed below, parquet files having more samples are generally more efficient, however a VCF or BCF file may only have 1000 samples, such that transposed files may be aggregated to generate larger sample size parquet files. In operation 610 the parquet formatted dosages are stored in a database. In some embodiments all of the above operations are performed by a genotype data module. In other embodiments, some operations may be performed by an imputed dosages module, such as generating imputed markers.

In some embodiments, an imputed dosages module may generate imputed dosages for an entire chromosome in a single process. In some embodiments, the imputed dosages are generated in a gene sequence variations file format, e.g., VCF, BCF, GEN, or BGEN. The imputed dosages data may then be converted to a parquet format in a single transposing process. In some implementations multiple parquet files may be generated for each batch of VCF/BCF files, as a VCF or BCF batch of files may comprise dosages for more than about 100,000 markers, while a parquet file may include dosages for less than about 100,000 markers.

Generally, individuals and samples may have a 1:1 relationship in the genotype data module when ingesting data from the imputed dosages module; however there can be multiple sample_ids referring to the same genotype_id, which can be a closer proxy for individual. Each set of dosages (based on, e.g., sample swaps or recomputing imputed dosages) associated with an individual may be referred to as a "sample_id," while an individual may have only a single "genotype_id." When clients request dosages for a given genotype_id from the genotype data module, the dosages from the latest of all sample_ids tied to the given genotype_id would be returned by default. This many:one relationship between sample_ids:genotype_ids can be useful for some of the time travel capabilities discussed further below.

As noted above, a VCF file may include about 1000 samples. In some embodiments, a parquet file has many more samples, e.g., about 1 million samples. Thus, to facilitate converting from VCF to parquet file formats, an importer module may be part of the genotype data module 112 to import and convert the sample and marker data from multiple VCF files to a parquet format. In some embodiments imports are performed using an importer shown in FIG. 5. One genotype_import is a grouping of multiple IRS batch_id imports. genotype_import_batch tracks the status of each of these VCF batches that are part of a genotype sample import. The maximum number of VCF batch IDs included as part of an import may be configurable.

In some embodiments the data pipeline can be orchestrated using a step function. The metadata required for the pipeline may be stored in relational database tables (e.g., RDS MySQL tables). The temporary and final parquet files powering the genotype data system may be stored in a cloud server or other storage.

Genotype Metadata and Operational Metadata

Figure 7:
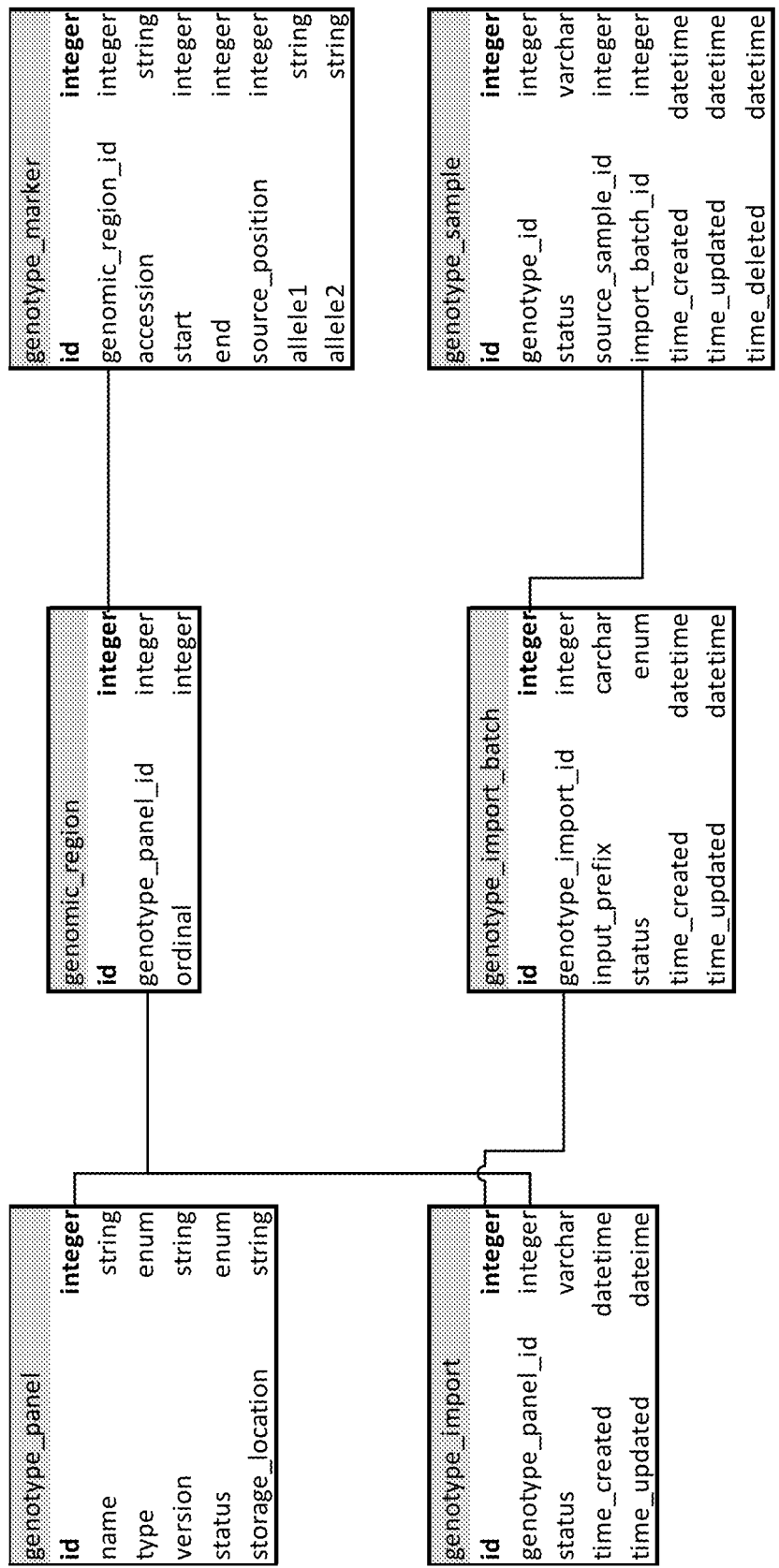
FIG. 7 illustrate exemplary metadata information.

A variety of different metadata may be used with the methods described herein. Metadata tables which can be shared by the data pipeline and the data-access layer to write and query the parquet files are described herein. FIG. 7 illustrates examples of metadata and metadata flows.

Examples of metadata used in various implementations along with their description are as follows:

genotype_panel: Metadata about the various imputation panels genomic_region: Metadata about genomic regions in panels genotype_marker: Metadata about the possible markers genotype_sample: Metadata about the imputed sample. Every import of a sample will generate a new genotype_sample_id. A genotype_id could have more than one genotype_sample_ids.

status: GDPR status of the sample. 'A' (ACTIVE)|'D' (DELETED)

time_created: time of import (this will represent the time of imputation of the sample)

time_updated: time of update (used to track updates to status) time deleted: time of GDPR delete genotype_import: Metadata about one genotype import. One import will be a collection of VCF/BCF batches.

genotype_import_batch: Metadata about each batch inside an import.

Parquet File (Parquet File Schema)

In some implementations, the parquet file stores the genotype sample id and the dosage values as a means of reducing overall size of the stored data and also choosing not to duplicate data that is available in the metadata layer. In some implementations, additional data may be stored alongside the dosage data (for example, genotype_id or date_created) in order to allow for rowgroup-level predicate pushdown (i.e., skipping rowgroups of data at read time based on the values of these columns). Predicate pushdown is a feature of the parquet spec that the system can support in some instances.

sample_id: references id in genotype_sample table marker_id (s): references the id in Marker table Optionally—genotype_id:

Optionally—date_created: date of imputation of the sample.

Batch Process for Converting VCF Files to Parquet

In some implementations, the transpose operation performed at 606 above results in parquet files written to a temporary 1000×1000 parquet files. The 1000×1000 parquet files for all the batches may be placed inside the corresponding genomic region under an import id. Before transposing, the marker_id's within a genomic region may be ordered based on their position for consistent ordering of the columns across all files. The markers may typically be sequentially ordered although in some implementations different orders can be used.

In some embodiments an example parquet file dimension is 1 million samples and 1000 markers per genomic region. A batch job may aggregate smaller parquet files. To achieve 1 million samples, the pipeline may need 1000 VCF/BCF batches. Thus, in some embodiments 1000 smaller parquet files is appropriate to generate parquet files of the desired dimension.

Ordering of the sample_ids across all genomic regions may be consistent with the ordering of genotype_sample_id in the metadata table. To ensure this, the aggregated data may be ordered based on the genotype_sample_id before writing the staged parquet file.

In some embodiments, the 1000×1000 parquet files for all the batches are placed inside the corresponding genomic region under the import id. Before transposing, the marker_id's within a genomic region are ordered based on its position for consistent ordering of the columns across all files. The markers are typically sequentially ordered although in some implementations different orders can be used.

Compactions

As part of recurring incremental runs, e.g., weekly, biweekly, monthly, etc., new parquet files may be created by the data pipelines. As an example, each incremental run processes only a few thousands of samples and as a result, the files generated by these jobs may be much smaller than the desired dimensions for a desired Parquet file dimension.

A benefit of writing separate parquet files during incremental runs is that operationally it's a much simpler process compared to appending samples to the "last" file. Generally during validation runs the read throughput doesn't suffer much because of small files. However, as the number of small files in a "genomic region" continues to grow, read throughput may suffer in the long run because small files will result in clients scanning more metadata, processing smaller column chunks (i.e., more seeks) and more (proportional to the number of files in the genomic region) column chunks to combine on the client side.

In some implementations, to balance operational simplicity of incremental runs and read performance in the long run, a "compaction" job may run periodically and merge small files within a genomic region. The compaction job can run regularly or ad hoc. As an example, it may run every 1 to 12 months (e.g., every 6 months or at a cadence that is frequent enough for creating parquet files that satisfy the desired parquet file dimensions). The compaction process can find all parquet files since the last compaction and merge them to create a larger parquet file.

Time-Travel Support

Time-travel refers to reproducing a GWAS that was performed at a point in the past. This may be useful to confirm or check results from a previously performed GWAS. As the data analyzed for a GWAS affects the results, in some implementation it is useful to identify a cohort of samples that were likely used for the GWAS. In some implementations, this may be determined by applying date constraints. In some implementations, time-travel may be supported through metadata available in imputed dosages module 105 that may be used to identify the cohort of samples used for the prior GWAS. This approach provides a more simple solution for checking prior GWAS results versus creating snapshots. In some implementations, an individual can have different imputed data and/or genotype data associated with their account over time as data storage follows an "append-only" pattern. For example, the data for an individual customer can evolve over time. This can be caused by, e.g., chip upgrades, sample swaps, or any situation that would result in a recomputation of the imputed dosages for that particular individual. The recomputation can also use a different imputation panel that can yield different imputed dosages. Each set of dosages associated with an individual may be referred to as a "sample_id," while an individual has only a single "genotype_id." The design of genotype data module 112 and time-travel support allows for "versioned" retrieval of the data as it would appear at a particular datetime. The metadata (including GDPR information in the metadata) can ensure that the same cases/controls are put together to re-create the older GWAS with corresponding "sample_id." that was used for the older GWAS.

In some embodiments, samples may be added using an append-only rule, such that any individual (or genotype id) may have multiple sample ids (for various reasons as noted above). The genotype data module 112 may be able to efficiently fetch the data for an arbitrary set of individuals as it would have been returned at any particular datetime. This may support experimental reproducibility, making it easier to validate old studies but also to try new methodologies/analyses for comparison against datasets that would be identical to datasets used by older methodologies.

Figure 8:
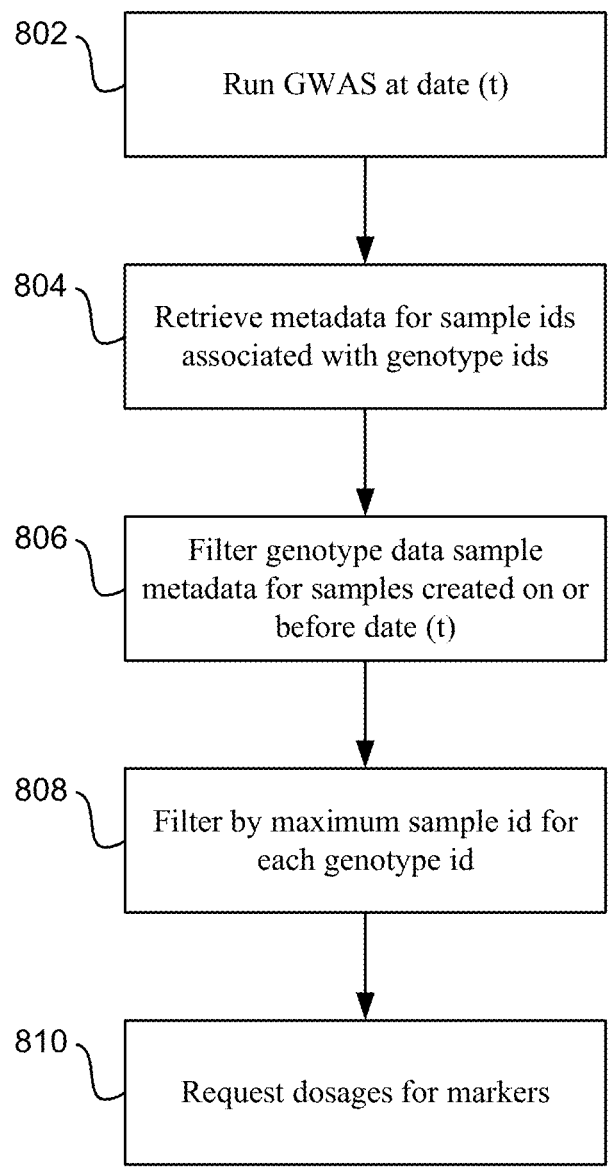
FIG. 8 presents a flowchart for "time-travelling" to replicate prior GWASes.

FIG. 8 presents a flowchart for implementing a time-travel query. In 802 a GWAS is performed at a datetime (t). Later, metadata for sample ids associated with genotype ids is retrieved (802). The genotype data sample metadata may be filtered for sample ids that were added prior to datetime (t) (806). As a new sample id is created for adding a new genotype data associated with a given individual, genotype data associated with sample ids created after the datetime (t) were not used for the GWAS and thus should not be retrieved. The metadata may also be filtered by maximum sample id for each genotype id, as the GWAS would be run on the variants associated with the latest sample id for a given individual/genotype id (808). In some embodiments imputed dosages may be determined for a given sample id. In such embodiments, the genotype id may also have an imputation id that corresponds with a set of imputed dosages and a datetime for the imputed dosages. In such embodiments, the metadata associated with imputation ids may also be used to filter the sample ids for the latest imputed dosages determined before datetime (t). The filtered sample ids and imputation ids may then be used to retrieve dosages (810).

GDPR Compliance

GDPR provides exemptions from hard deletion of customer data for scientific reproducibility. This exclusion may be applied to the imputed dosage storage in some implementations. The parquet datasets may be treated as "append-only" datasets in some implementations.

In some implementations, GDPR and other privacy related deletion requests can be handled in different ways. In some implementations, a GDPR deletion date can be added to the metadata tables to indicate deletion status. This attribute can be used to determine if and when an id should be part of a GWAS run or other data run. Updating the metadata with the GDPR deletion date can be useful for scientific reproducibility and time travel to confirm GWAS results obtained from data runs done prior to the GDPR deletion request.

In some implementations a new imputation-id can be assigned when a GDPR deletion is requested along with inserting a null row in the corresponding row for the user in the parquet files. In some cases, a parquet file has less than 1000 rows with genetic data from the deletion requests.

Experiments

Figure 9:
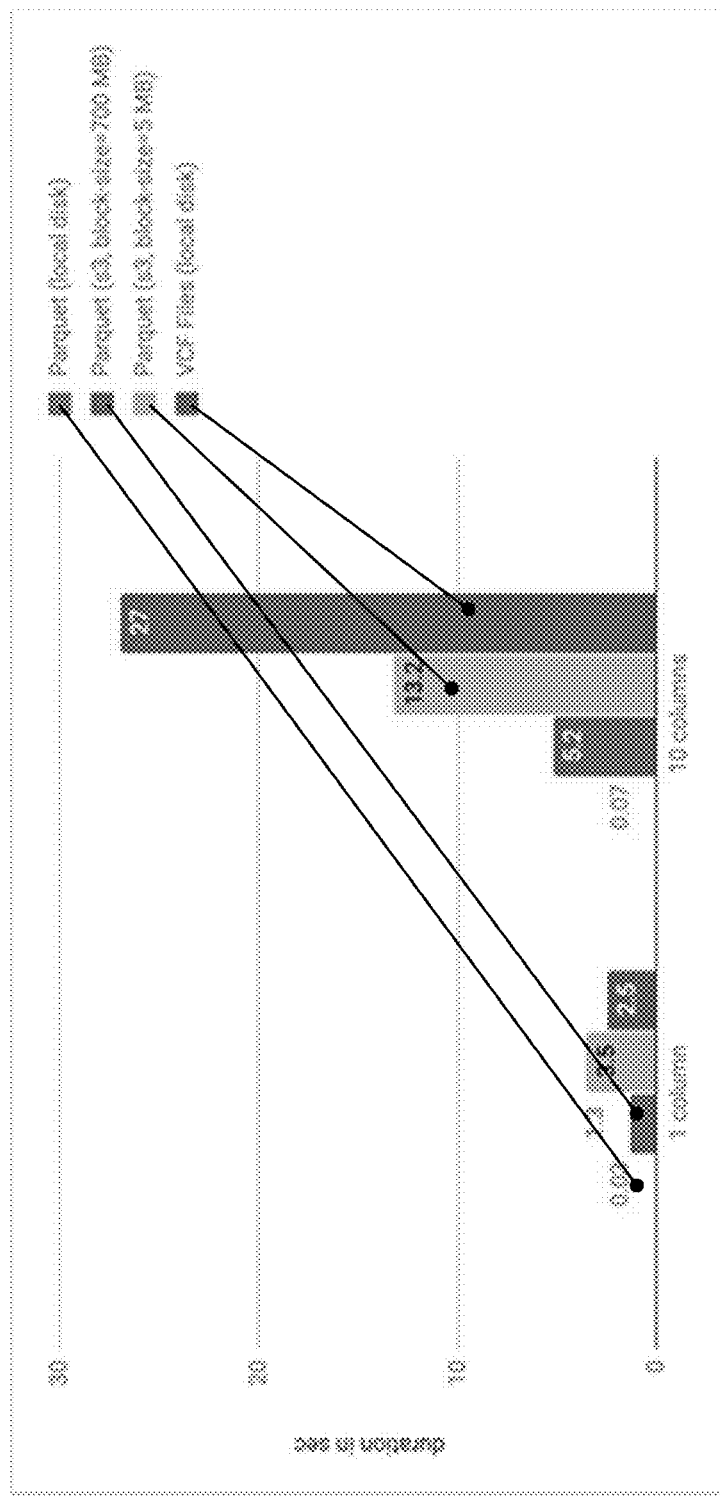
FIG. 9 illustrates comparison of query performance between VCF and Parquet for 1 and 10 columns.

FIG. 9 presents a comparison of query performance between VCF and Parquet files for 1 and 10 columns. To retrieve dosages for 1 million samples for a given marker, it took about 2.5 seconds using the VCF files and only 0.03 seconds to get the same data from Parquet files—nearly 80× faster. Experiments were also performed to compare the performance of queries against Parquet files stored in a cloud server using s3FS and PyArrow. In this case, the time taken to query the cloud-based Parquet file is 3.5 seconds. Performance of queries retrieving 10 markers similarly performed very well against the Parquet files, as shown in FIG. 9.

For these experiments, each VCF file has dosages for 1000 samples and over 200,000 markers and a Parquet file has dosages for 1 million samples and 1000 markers. In other words, a VCF file has 200 million dosages while a Parquet file has 1 billion dosages. For a database with roughly 10 million samples and 58 million markers, compressed VCF files take up roughly 600 TB of disk space compared to just 200 TB for the Parquet files.

These experiments were run on a c3.8xlarge AWS EC2 instance with 32 vCPU, 60G RAM, and a maximum of 10 Gigabit network throughput. Actual performance of the queries can vary significantly based on instance type. Before executing queries against the VCF file, a tabix index file (http://www.htslib.org/doc/tabix.html) was created using Pysam (https://pysam.readthedocs.io/en/latest/index.html) to enable fast random access to marker(s). Pysam is a python module for reading, manipulating, and writing genomic data sets, including VCF formatted files.

To further compare VCF and Parquet files, additional experiments to retrieve 100 and 1000 columns were performed and, in each case, Parquet outperformed VCF. The following table shows the results from these experiments:

TABLE 1

Results from comparing the performance of queries against VCF and Parquet

| File Format | Access Library | Storage | Block Size | Threads | List Columns | Number of samples = 1 million | | | |
|---|---|---|---|---|---|---|---|---|---|
| | | | | | | 1 column | 10 columns | 100 columns | 1 K columns |
| VCF Files | Pysam | local disk | na | no | na | 2.5 sec | 27 sec | 12 min | 5 hr |
| Parquet | PyArrow | local disk | na | no | yes | 0.03 sec | 0.07 sec | 0.6 sec | 6.15 sec |
| | | | na | yes | yes | 0.02 sec | 0.03 sec | 0.09 sec | 0.76 sec |
| | | | na | yes | no | na | na | na | 0.76 sec |
| | | s3 | default (5 MB) | no | yes | 3.5 sec | 13.2 sec | 96 sec | 17 min |
| | | | | yes | yes | 4.6 sec | 9.3 sec | 98 sec | 16 min |
| | | | 700 MB | yes | yes | 1.5 sec | 6 sec | 7 sec | 8.6 sec |
| | | | | no | yes | 1.3 sec | 5.2 sec | 7.5 sec | 15 sec |
| | | | | yes | no | na | na | na | 6.5 sec |

The performance of reading the Parquet files using a cloud server is significantly impacted by the 'default_block_size' property initialized as part of opening a cloud server connection (when using S3 storage service offered by Amazon Web Services). This property configures the number of bytes to read ahead during a 'seek( )' before closing and reopening the S3 HTTP connection. In some embodiments, the default value of 5 MB may be too small for large files. By setting this property to a high value, most of the file contents are prefetched and cached, thus cutting down the number of times a cloud connection is closed and reopened. Since opening and closing the connection are fairly expensive operations, in some implementations reading the majority of the file contents and discarding is cheaper than incrementally pre-fetching small blocks. In some implementations increasing the block size improves access pattern performance when working with object stores like S3. In some implementations, the block size is at least 100 MB, at least about 200 MB, at least about 250 MB, at least about 400 MB, at least about 500 MB, at least about 600 MB, or at least about 700 MB. With a larger block size, scanning the Parquet file with 1000 markers using PyArrow/s3FS (without multithreading) is over 1000× faster than with VCF files.

In some implementations, in addition to the block size, enabling the 'use_threads' option in PyArrow cut down the query execution time from 15 seconds to 8.6 seconds for 1000 markers. In some implementations, performance may be improved by skipping the 'columns' argument entirely compared to listing of every column. This approach further cut down the overall query execution time from 8.6 seconds to 6.5 seconds. Query performance was also analyzed when reading Parquet files from the local disk. As shown in the table above, queries are extremely fast when reading from local disk—reading 1000 markers with 1 million samples took less than 1 second.

Figure 10:
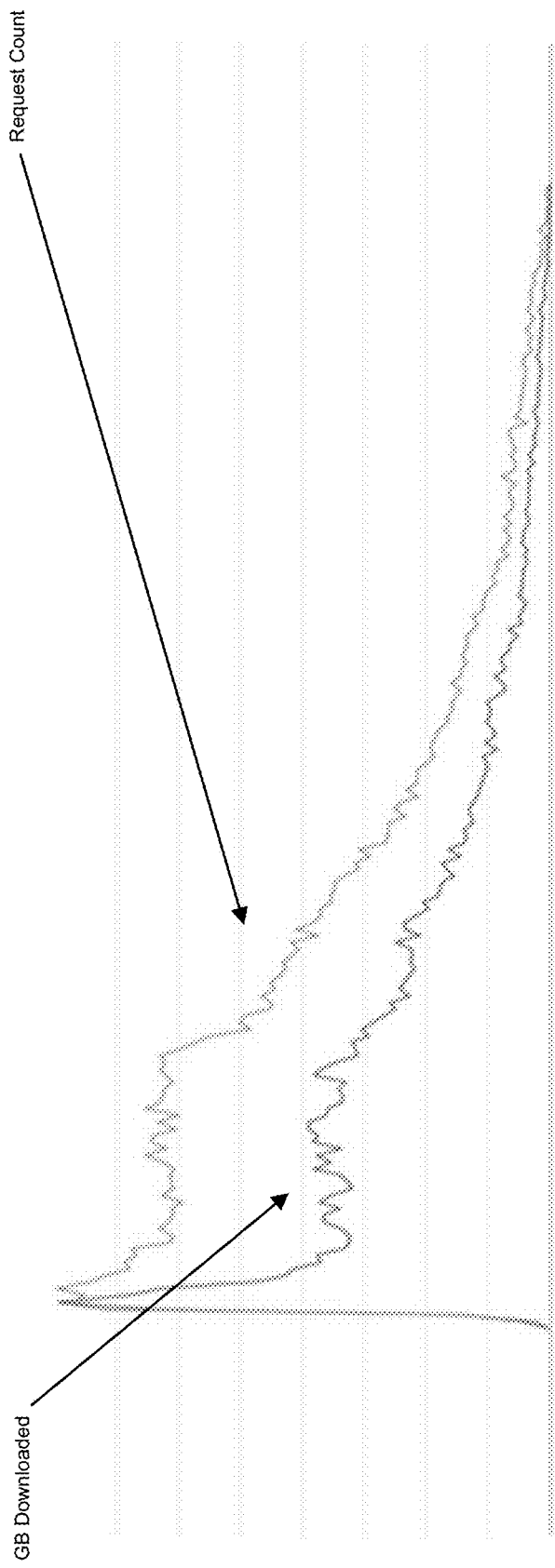
FIGS. 10 and 11 illustrate performance data for pulling data from the Genotype module.
Figure 11:
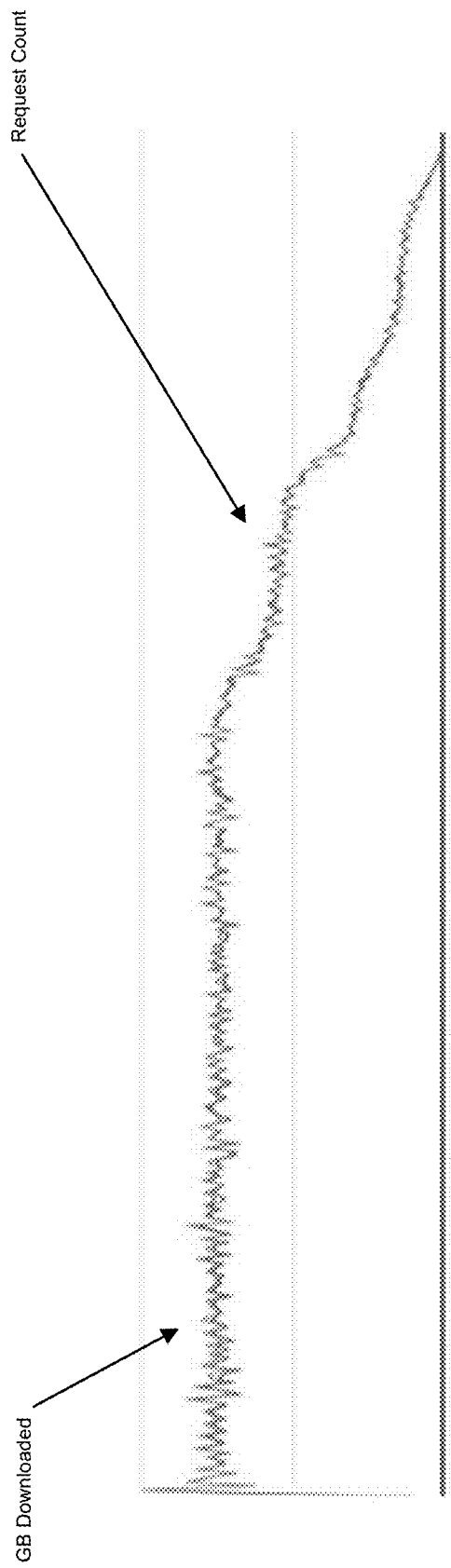

FIG. 10 presents a chart of GB downloaded and Request Count for an experiment pulling data from a genetic data storage module 112 as described herein for a GWAS on cluster headaches. 1.4M markers were requested for 1M samples. 1404 parquet files were scanned, with more than 129,000,000 dosages read per second and about 4,000 requests per minute. FIG. 11 presents a chart of GB downloaded and Request Count from a genetic data storage module as described herein for a GWAS on migraines. 1.4M markers were requested for 8.5M samples, with 12.6 thousand parquet files scanned and about 18,000 requests per minute. In some implementations, a genetic data storage system described herein may be used to request at least about 500, at least about 1,000, at least about 2,000, at least about 3,000, at least about 4,000, or at least about 5,000 requests per second. In some implementations, the requests per second may be further multiplied by the number of partitions or cloud servers that can provided dosages. In some implementations, more than 1, at least about 5, or at least about 10 cloud servers may contain distributed parquet files that may be queried to request dosage information, multiplying the number of requests per second by the number of servers.

Computational Embodiments

Figure 12:
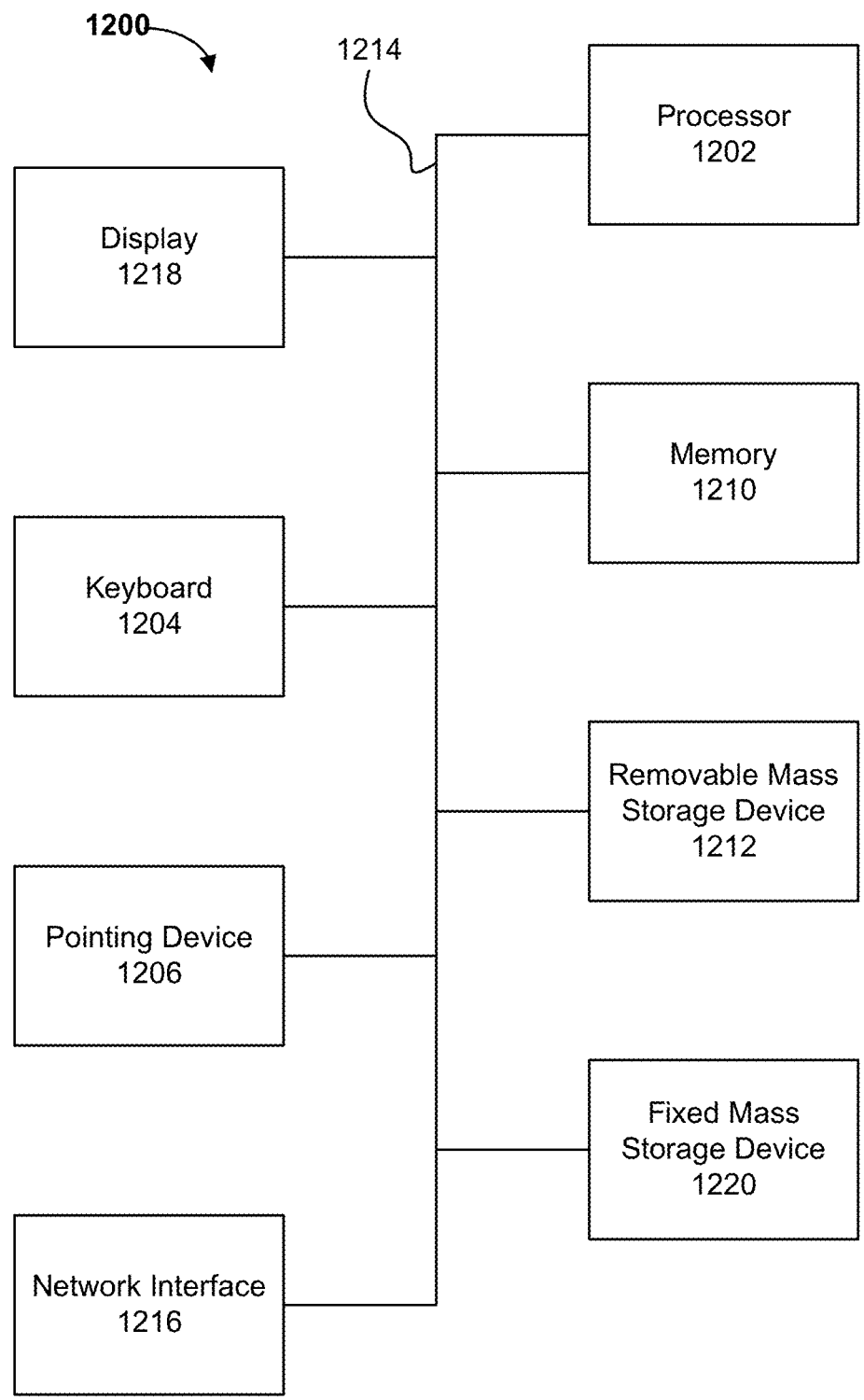
FIG. 12 presents an example computer system that may be employed to implement certain embodiments herein.

FIG. 12 is a functional diagram illustrating a programmed computer system for converting file formats, storing, and retrieving genotype data in accordance with some embodiments. As will be apparent, other computer system architectures and configurations can be used to store and retrieve genotype data. Computer system 1200, which includes various subsystems as described below, includes at least one microprocessor subsystem (also referred to as a processor or a central processing unit (CPU)) 1202. For example, processor 1202 can be implemented by a single-chip processor or by multiple processors. In some embodiments, processor 1202 is a general purpose digital processor that controls the operation of the computer system 1200. Using instructions retrieved from memory 1210, the processor 1202 controls the reception and manipulation of input data, and the output and display of data on output devices (e.g., display 1218). In some embodiments, processor 102 includes and/or is used to implement the flowchart of FIG. 12.

Processor 1202 is coupled bi-directionally with memory 1210, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 1202. Also as is well known in the art, primary storage typically includes basic operating instructions, program code, data, and objects used by the processor 1202 to perform its functions (e.g., programmed instructions). For example, memory 1210 can include any suitable computer readable storage media, described below, depending on whether, for example, data access needs to be bi-directional or uni-directional. For example, processor 1202 can also directly and very rapidly retrieve and store frequently needed data in a cache memory (not shown).

A removable mass storage device 1212 provides additional data storage capacity for the computer system 1200, and is coupled either bi-directionally (read/write) or uni-directionally (read only) to processor 1202. For example, storage 1212 can also include computer readable media such as magnetic tape, flash memory, PC-CARDS, portable mass storage devices, holographic storage devices, and other storage devices. A fixed mass storage device 1220 can also, for example, provide additional data storage capacity. The most common example of mass storage 1220 is a hard disk drive. Mass storage 1212 and 1220 generally store additional programming instructions, data, and the like that typically are not in active use by the processor 1202. It will be appreciated that the information retained within mass storage 1212 and 1220 can be incorporated, if needed, in standard fashion as part of memory 1210 (e.g., RAM) as virtual memory.

In addition to providing processor 1202 access to storage subsystems, bus 1214 can be used to provide access to other subsystems and devices. As shown, these can include a display monitor 1218, a network interface 1216, a keyboard 1204, and a pointing device 1206, as well as an auxiliary input/output device interface, a sound card, speakers, and other subsystems as needed. For example, the pointing device 1206 can be a mouse, stylus, track ball, or tablet, and is useful for interacting with a graphical user interface.

The network interface 1216 allows processor 1202 to be coupled to another computer, computer network, or telecommunications network using a network connection as shown. For example, through the network interface 1216, the processor 1202 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 1202 can be used to connect the computer system 1200 to an external network and transfer data according to standard protocols. For example, various process embodiments disclosed herein can be executed on processor 1202, or can be performed across a network such as the Internet, intranet networks, or local area networks, in conjunction with a remote processor that shares a portion of the processing. Additional mass storage devices (not shown) can also be connected to processor 1202 through network interface 1216.

An auxiliary I/O device interface (not shown) can be used in conjunction with computer system 1200. The auxiliary I/O device interface can include general and customized interfaces that allow the processor 1202 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer readable medium is any data storage device that can store data which can thereafter be read by a computer system. Examples of computer readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 12 is but an example of a computer system suitable for use with the various embodiments disclosed herein. Other computer systems suitable for such use can include additional or fewer subsystems. In addition, bus 1214 is illustrative of any interconnection scheme serving to link the subsystems. Other computer architectures having different configurations of subsystems can also be utilized.

Conclusion

In the description above, for purposes of explanation only, specific nomenclature is set forth to provide a thorough understanding of the present disclosure. However, it will be apparent to one skilled in the art that these specific details are not required to practice the teachings of the present disclosure.

The language used to disclose various embodiments describes, but should not limit, the scope of the claims. For example, in the previous description, for purposes of clarity and conciseness of the description, not all of the numerous components shown in the figures are described. The numerous components are shown in the drawings to provide a person of ordinary skill in the art a thorough, enabling disclosure of the present specification. The operation of many of the components would be understood and apparent to one skilled in the art. Similarly, the reader is to understand that the specific ordering and combination of process actions described is merely illustrative, and the disclosure may be performed using different or additional process actions, or a different combination of process actions.

Each of the additional features and teachings disclosed herein can be utilized separately or in conjunction with other features and teachings for storing, retrieving, and analyzing genotype data. Representative examples using many of these additional features and teachings, both separately and in combination, are described in further detail with reference to the attached drawings. This detailed description is merely intended for illustration purposes to teach a person of skill in the art further details for practicing preferred aspects of the present teachings and is not intended to limit the scope of the claims. Therefore, combinations of features disclosed in the detailed description may not be necessary to practice the teachings in the broadest sense, and are instead taught merely to describe particularly representative examples of the present disclosure. Additionally and obviously, features may be added or subtracted as desired without departing from the broader spirit and scope of the disclosure. Accordingly, the disclosure is not to be restricted except in light of the attached claims and their equivalents.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

None of the pending claims includes limitations presented in "means plus function" or "step plus function" form. (See, 35 USC § 112(f)). It is Applicant's intent that none of the claim limitations be interpreted under or in accordance with 35 U.S.C. § 112(f).

What is claimed is:

1. A method of providing information from one or more files to a database having a table with at least about 20 million columns, the method comprising:
   receiving, by a processor from a storage device, one or more Variant Call Format (VCF) or Binary Variant Call Format (BCF) files comprising imputed genetic data for one or more individuals, wherein the imputed genetic data is in a columnar format, wherein the imputed genetic data includes greater than about 20 million markers for each of the one or more individuals, and wherein the greater than about 20 million markers are in sequential order;
   transposing, by the processor, the imputed genetic data from the one or more VCF or BCF files for each of the one or more individuals from columnar format to a plurality of rows, wherein the imputed genetic data for each of the one or more individuals is included in a row for the corresponding individuals; and
   sending, by the processor, the transposed imputed genetic data to the storage device to be stored in the database with a unique column corresponding to each of the greater than about 20 million markers for each of the one or more individuals and a unique row for each of the one or more individuals.

2. The method of claim 1, wherein the imputed genetic data includes greater than about 50 million markers for each of the one or more individuals.

3. The method of claim 1, wherein the storage device comprises a magnetic tape, a flash memory, a PC-CARD, a portable mass storage device, a holographic storage device, a hard disk drive, a hard disk, a floppy disk, a magnetic tape, an optical media, a magneto-optical media, an application-specific integrated circuit (ASIC), a programmable logic device (PLD), a read-only memory (ROM), or a random-access memory (RAM).

4. The method of claim 1, wherein the storage device comprises a cloud server.

5. The method of claim 4, wherein sending the transposed imputed genetic data to the storage device comprises outputting information to the storage device via a network interface.

6. The method of claim 1, wherein the database includes greater than about 10 million individuals and greater than about 10 million rows.

7. The method of claim 1, wherein the database includes greater than about 10 million individuals and greater than about 20 million rows.

8. The method of claim 1, wherein the database includes greater than about 10 million individuals and greater than about 30 million rows.

9. The method of claim 1, further comprising:
accessing, by the processor, a row of user data for an individual; and
generating, by the processor, user facing content for the individual based on the accessed user data.

10. The method of claim 1, further comprising:
accessing, by the processor, the database to identify genetic data for a plurality of the one or more individuals having one or more preselected phenotypes;
assembling, by the processor, a cases cohort comprising a first plurality of individuals having the one or more preselected phenotypes;
assembling, by the processor, a control cohort comprising a second plurality of individuals not in the cases cohort; and
performing, by the processor, a genome wide association study (GWAS) based on the genetic data from the database for individuals in the cases cohort and control cohort.

11. The method of claim 1, further comprising, prior to receiving one or more VCF or BCF files:
imputing, by the processor, the genetic data of the one or more individuals; and
sending, by the processor, the imputed genetic data to the storage device to be stored in the one or more VCF or BCF files.

12. The method of claim 11, wherein sending the imputed genetic data in the one or more VCF or BCF files is done in one or more batches.

13. The method of claim 1, wherein sending the transposed imputed genetic data to the storage device to be stored in the database is done in one or more batches.

14. The method of claim 1, further comprising:
generating, by the processor, metadata based on an imputation process used to generate the imputed genetic data, including an imputation panel version used for the imputation process; and
storing, by the processor, the metadata.

15. The method of claim 1, further comprising:
storing, by the processor, metadata based on the receiving, transposing, and sending steps; and
sending, by the processor, the metadata to the storage device to be stored in the database.

16. The method of claim 1, wherein the database includes a plurality of tables having dimensions of at least about 1 million×1 million.

17. The method of claim 1, further comprising:
receiving, by the processor, a request from a user to delete the user's genetic data; and
responsive to the request from the user, updating, by the processor, metadata for the corresponding user's genetic data so that the user's genetic data is not used in future data processing activities.

18. The method of claim 1, further comprising:
receiving, by the processor, a request from a user to delete the user's genetic data; and
responsive to the request from the user, deleting or nulling, by the processor, the imputed genetic data for the corresponding user's data.

19. A system configured to provide information from one or more files to a database having a table with at least about 20 million columns, the system comprising:
a processor; and
a storage device,
wherein the system is configured to:
receive, by the processor from the storage device, one or more Variant Call Format (VCF) or Binary Variant Call Format (BCF) files comprising imputed genetic data for one or more individuals, wherein the imputed genetic data is in a columnar format, wherein the imputed genetic data includes greater than about 20 million markers for each of the one or more individuals, and wherein the greater than about 20 million markers are in sequential order;
transpose, by the processor, the imputed genetic data from the one or more VCF or BCF files for each of the one or more individuals from columnar format to a plurality of rows, wherein the imputed genetic data for each of the one or more individuals is included in a row for the corresponding individuals; and
send, by the processor, the transposed imputed genetic data to the storage device to be stored in the database with a unique column corresponding to each of the greater than about 20 million markers for each of the one or more individuals and a unique row for each of the one or more individuals.

20. The system of claim 19, wherein the imputed genetic data includes greater than about 50 million markers for each of the one or more individuals.

21. The system of claim 19, wherein the storage device comprises a magnetic tape, a flash memory, a PC-CARD, a portable mass storage device, a holographic storage device, a hard disk drive, a hard disk, a floppy disk, a magnetic tape, an optical media, a magneto-optical media, an application-specific integrated circuit (ASIC), a programmable logic device (PLD), a read-only memory (ROM), or a random-access memory (RAM).

22. The system of claim 19, wherein the storage device comprises a cloud server.

23. The system of claim 22, wherein the system further comprises a network interface, and wherein sending the transposed imputed genetic data to the storage device comprises outputting information to the storage device via the network interface.

24. The system of claim 19, wherein the database includes greater than about 10 million individuals and greater than about 10 million rows.

* * * * *